United States Patent
Satake et al.

(10) Patent No.: US 9,650,473 B2
(45) Date of Patent: May 16, 2017

(54) POLYSILOXANE-BASED MACROMONOMER FOR OPHTHALMIC LENS AND OPHTHALMIC LENS USING THE SAME

(71) Applicants: MENICON CO., LTD., Nagoya-shi, Aichi (JP); SHIN-ETSU CHEMICAL CO., LTD., Tokyo (JP)

(72) Inventors: Kohsuke Satake, Kasugai (JP); Shoji Ichinohe, Annaka (JP)

(73) Assignees: MENICON CO., LTD., Nagoya-shi (JP); SHIN-ETSU CHEMICAL CO., LTD., Tokyo (JP)

( * ) Notice: Subject to any disclaimer, the term of this patent is extended or adjusted under 35 U.S.C. 154(b) by 0 days.

(21) Appl. No.: 15/171,678

(22) Filed: Jun. 2, 2016

(65) Prior Publication Data

US 2016/0272766 A1    Sep. 22, 2016

Related U.S. Application Data

(63) Continuation of application No. PCT/JP2013/083670, filed on Dec. 16, 2013.

(51) Int. Cl.
| | |
|---|---|
| C08G 77/20 | (2006.01) |
| C08G 77/46 | (2006.01) |
| C08G 18/61 | (2006.01) |
| C08G 18/67 | (2006.01) |
| C08G 18/75 | (2006.01) |
| C08G 18/81 | (2006.01) |
| C08L 83/12 | (2006.01) |
| G02B 1/04 | (2006.01) |
| C08F 290/06 | (2006.01) |
| A61F 2/16 | (2006.01) |

(52) U.S. Cl.
CPC .......... *C08G 77/46* (2013.01); *C08F 290/068* (2013.01); *C08G 18/61* (2013.01); *C08G 18/672* (2013.01); *C08G 18/755* (2013.01); *C08G 18/8116* (2013.01); *C08L 83/12* (2013.01); *G02B 1/043* (2013.01); *A61F 2/16* (2013.01)

(58) Field of Classification Search
CPC ........ C08G 77/46; C08G 77/20; C08G 18/61; C08G 18/672; C08G 18/755; C08L 83/12
See application file for complete search history.

(56) References Cited

U.S. PATENT DOCUMENTS

| 6,140,438 | A  | 10/2000 | Ojio et al. |
| 8,124,668 | B2 | 2/2012 | Baba et al. |
| 2002/0005933 | A1 | 1/2002 | Imafuku |
| 2004/0014898 | A1 | 1/2004 | Ichihara |
| 2006/0142410 | A1 | 6/2006 | Baba et al. |
| 2009/0212450 | A1 | 8/2009 | Imafuku |
| 2010/0119744 | A1 | 5/2010 | Yokoyama et al. |
| 2012/0252925 | A1 | 10/2012 | Iwata et al. |
| 2013/0053511 | A1* | 2/2013 | Rashid ............... C08G 18/4829 524/588 |
| 2015/0011667 | A1* | 1/2015 | Saxena .................. C08G 77/20 522/13 |
| 2016/0185914 | A1* | 6/2016 | Ueyama ................. C08G 77/46 556/437 |

FOREIGN PATENT DOCUMENTS

| JP | H06-230320 A | 8/1994 |
| JP | H08-208761 A | 8/1996 |
| JP | H08-227001 A | 9/1996 |
| JP | H10-75971 A | 3/1998 |
| JP | 2001-072739 A | 3/2001 |
| JP | 2001-311917 A | 11/2001 |
| JP | 2004-037811 A | 2/2004 |
| JP | 2005-089654 A | 4/2005 |
| JP | 3641110 B2 | 4/2005 |
| JP | 2007-070405 A | 3/2007 |
| JP | 2008-511870 A | 4/2008 |
| JP | 4235204 B2 | 3/2009 |
| JP | 2010-020330 A | 1/2010 |
| JP | 2011-219512 A | 11/2011 |
| JP | 2012-513042 A | 6/2012 |
| WO | 96/31792 A1 | 10/1996 |
| WO | 2004/063795 A1 | 7/2004 |
| WO | 2010/071691 A1 | 6/2010 |

OTHER PUBLICATIONS

Mar. 18, 2014 Search Report issued in International Patent Application PCT/JP2013/083671.
Mar. 18, 2014 Writen Opinion of the International Searching Authority issued in International Patent Application No. PCT/JP2013/083671.
U.S. Appl. No. 15/177,781, filed Jun. 9, 2016 in the name of Kohsuke Satake.
Mar. 18, 2014 International Preliminary Report on Patentability issued in International Patent Application No. PCT/JP2013/083670.
Mar. 18, 2014 International Search Report issued in International Patent Application No. PCT/JP2013/083670.
Oct. 3, 2016 Office Action issued in U.S. Appl. No. 15/177,781.
Sep. 27, 2016 Office Action issued in U.S. Appl. No. 15/177,781.

* cited by examiner

*Primary Examiner* — Margaret Moore
(74) *Attorney, Agent, or Firm* — Oliff PLC

(57) ABSTRACT

A polysiloxane-based macromonomer for an ophthalmic lens, which exhibits excellent compatibility with respect to a hydrophilic component such as a hydrophilic monomer. The polysiloxane-based macromonomer has at least one polymerizable group, a polysiloxane chain having a siloxane unit as a repeating unit, a polyoxyethylene chain in which a number of repetition of an oxyethylene group is two or more, and a polyoxyalkylene chain having an oxyalkylene group other than the oxyethylene group as a repeating unit, wherein an HLB value calculated according to a formula: [HLB value]=E/5 is within a range from 0.7 to 6.0, wherein E represents a weight fraction (wt %) of the oxyethylene group in a molecule of the polysiloxane-based macromonomer.

11 Claims, No Drawings

POLYSILOXANE-BASED MACROMONOMER FOR OPHTHALMIC LENS AND OPHTHALMIC LENS USING THE SAME

CROSS REFERENCE TO RELATED APPLICATION

This application is a continuation of the International Application No. PCT/JP2013/083670 filed on Dec. 16, 2013, the entireties of which are incorporated herein by reference.

BACKGROUND OF THE INVENTION

Field of the Invention

The present invention relates to a polysiloxane-based macromonomer for an ophthalmic lens and an ophthalmic lens using the same, and more particularly relates to a polysiloxane-based macromonomer for an ophthalmic lens, which exhibits excellent compatibility with a hydrophilic monomer, and which permits use of various composition in production of an ophthalmic lens.

Description of Related Art

Various properties are required for an ophthalmic lens such as a contact lens and an intraocular lens. In recent years, the contact lens, in particular, is required to exhibit more excellent oxygen permeability so that a sufficient amount of oxygen is supplied to a cornea of the eye.

On the other hand, it is widely known that a silicone polymer having a siloxane main chain including a siloxane unit as a repeating unit has excellent oxygen permeability. Various kinds of silicone polymer have been used as materials of various kinds of ophthalmic lens including the contact lens. For instance, a copolymer (silicone hydrogel) of a polysiloxane-based macromonomer in which a polymerizable group is bonded to the siloxane main chain, and a hydrophilic monomer such as N-vinylpyrrolidone and dimethyl acrylamide gives a highly oxygen-permeable water-absorptive lens. Accordingly, various studies have been made and various techniques have been proposed regarding the ophthalmic lens (particularly, contact lens) formed of the silicone hydrogel, and a method of production of such an ophthalmic lens. Specifically, a silicone hydrogel contact lens is proposed in JP-T-2008-511870, an ophthalmic lens for long-term wearing is proposed in JP-A-2010-20330 and a method of production of a silicone hydrogel contact lens is proposed in JP-T-2012-513042.

However, it cannot be said that the conventional polysiloxane-based macromonomer such as those described in the above-indicated Patent Documents 1 to 3 exhibits sufficiently high compatibility with the hydrophilic monomer. Therefore, in production of the ophthalmic lens using the conventional polysiloxane-based macromonomer, and the hydrophilic monomer or the like, there is a risk that when the components are mixed together, the mixture is clouded or whitened, or a polymer obtained by polymerization is clouded or whitened, depending on a combination of the components, giving rise to a problem that the combination of the components is limited in order to obtain a transparent ophthalmic lens.

SUMMARY OF THE INVENTION

The present invention was made in view of the background art described above. It is an object of the invention to provide a polysiloxane-based macromonomer for an ophthalmic lens, which exhibits excellent compatibility with a hydrophilic component such as a hydrophilic monomer. Other objects of the invention are to provide an ophthalmic lens and to provide a contact lens, by using the above-described polysiloxane-based macromonomer for an ophthalmic lens.

The above-described object can be achieved according to a principle of the invention, which provides a polysiloxane-based macromonomer for an ophthalmic lens, characterized by including at least one polymerizable group, a polysiloxane chain having a siloxane unit as a repeating unit, a polyoxyethylene chain in which a number of repetition of an oxyethylene group is two or more, and a polyoxyalkylene chain having an oxyalkylene group other than the oxyethylene group as a repeating unit, wherein an HLB value calculated according to the following formula is within a range from 0.7 to 6.0:

$$[\text{HLB value}] = E/5$$

wherein E represents a weight fraction (wt %) of the oxyethylene group in a molecule of the polysiloxane-based macromonomer.

According to a first preferable form of the polysiloxane-based macromonomer for the ophthalmic lens according to the invention, the HLB value is within a range from 1.0 to 5.0.

According to a second preferable form of the polysiloxane-based macromonomer for the ophthalmic lens according to the invention, the number of repetition of the oxyethylene group is within a range from 4 to 15.

According to a third preferable form of the polysiloxane-based macromonomer for the ophthalmic lens according to the invention, the polyoxyalkylene chain is a polyoxypropylene chain having an oxypropylene group as a constituent unit.

According to a fourth preferable form of the polysiloxane-based macromonomer for the ophthalmic lens according to the invention, a number of repetition of the oxypropylene group is within a range from 5 to 16.

According to a fifth preferable form of the polysiloxane-based macromonomer for the ophthalmic lens according to the invention, the at least one polymerizable group is bonded to the polysiloxane chain constituting a main chain of a molecule of the polysiloxane-based macromonomer, through at least one urethane bond.

On the other hand, the present invention also provides an ophthalmic lens and a contact lens, which are formed of a polymer of a polymerizable composition including the polysiloxane-based macromonomer for an ophthalmic lens according to the above-described forms.

As described above, the polysiloxane-based macromonomer for an ophthalmic lens according to the invention is configured so as to have in its molecule, the polyoxyethylene chain in which the number of repetition of the oxyethylene group is two or more and the polyoxyalkylene chain having the oxyalkylene group other than the oxyethylene group, as the repeating unit, and such that the HLB value calculated according to the predetermined formula is held within the range from 0.7 to 6.0. Accordingly, the polysiloxane-based macromonomer according to the invention exhibits significantly improved compatibility with respect to a hydrophilic monomer, as compared with that of the conventional polysiloxane-based macromonomer, while securing the same degree of compatibility with respect to a hydrophobic monomer, as that of the conventional polysiloxane-based macromonomer.

Therefore, the polysiloxane-based macromonomer according to the invention can be used in combination with the other components, which combination could not be employed for the conventional polysiloxane-based macromonomer due to its poor compatibility with the hydrophilic monomer, to permit production of an ophthalmic lens having more excellent degrees of oxygen permeability and various mechanical properties, for example. Further, the polysiloxane-based macromonomer according to the invention is expected to permit production of the ophthalmic lens, particularly a contact lens, having various properties, since the polysiloxane-based macromonomer according to the invention can be used together with the other components which could not be used together with the conventional polysiloxane-based macromonomer.

DETAILED DESCRIPTION OF THE INVENTION

By the way, a polysiloxane-based macromonomer for an ophthalmic lens (hereinafter also simply referred to as "polysiloxane-based macromonomer") according to the invention has: at least one polymerizable group; a polysiloxane chain having a siloxane unit as a repeating unit; a) a polyoxyethylene chain in which a number of repetition of an oxyethylene group ($—CH_2CH_2O—$) is two or more; and b) a polyoxyalkylene chain having an oxyalkylene group other than the oxyethylene group, as a repeating unit. The polysiloxane-based macromonomer according to the invention is configured such that an HLB value calculated according to the following formula is held within a range from 0.7 to 6.0:

[HLB value]=$E/5$ wherein E represents a weight fraction (wt %) of the oxyethylene group in a molecule of the polysiloxane-based macromonomer.

As described above, the polysiloxane-based macromonomer according to the invention is configured so as to have the specific polyoxyethylene chain and the polyoxyalkylene chain other than the polyoxyethylene chain, and such that the HLB value calculated according to the above-indicated formula is held within the predetermined range, whereby the polysiloxane-based macromonomer according to the invention can exhibit good compatibility with respect to both of a hydrophobic monomer and a hydrophilic monomer, which have been generally used in production of an ophthalmic lens. Accordingly, in production of various kinds of ophthalmic lens including the contact lens, the polysiloxane-based macromonomer according to the invention can be used in combination with the other components (particularly with the hydrophilic monomer), which combination has been difficult to be employed for the conventional polysiloxane-based macromonomer due to its compatibility with the other components. Therefore, the polysiloxane-based macromonomer for the ophthalmic lens according to the invention is expected to permit production of the ophthalmic lens having more excellent properties such as oxygen permeability, as compared with the case of use of the conventional polysiloxane-based macromonomer. Further, the polysiloxane-based macromonomer according to the invention is expected to permit production of the ophthalmic lens having various properties, since the polysiloxane-based macromonomer according to the invention can be used together with the other components which could not be used together with the conventional polysiloxane-based macromonomer.

The polysiloxane-based macromonomer according to the invention has the polymerizable group similar to that of the conventional polysiloxane-based macromonomer. Examples of the polymerizable group include an acryloyloxy group, a methacryloyloxy group, a vinyl group and an allyl group.

The polysiloxane-based macromonomer according to the invention has the polyoxyethylene chain in which the number of repetition of the oxyethylene group is two or more. In this respect, it is noted that where the number of repetition of the oxyethylene group is excessively large (excessively high), it is difficult to produce the monomer. Further, where the macromonomer has the polyoxyethylene chain having an excessively large (excessively high) number of repetition of the oxyethylene group, there is a risk that the ophthalmic lens obtained by using the macromonomer is fragile and has a low degree of strength. Therefore, the number of repetition of the oxyethylene group constituting the polyoxyethylene chain of the polysiloxane-based macromonomer for the ophthalmic lens according to the invention is selected preferably within a range from 4 to 15, and more preferably within a range from 4 to 10.

On the other hand, the polysiloxane-based macromonomer according to the invention has the polyoxyalkylene chain having the oxyalkylene group other than the oxyethylene group, as the repeating unit, as well as the polyoxyethylene chain in which the number of repetition of the oxyethylene group is two or more. The oxyalkylene group of the polyoxyalkylene chain may be any one of various known oxyalkylene groups, as long as effects of the invention can be achieved by employing the oxyalkylene group. Specific examples of the oxyalkylene group include an oxypropylene group and an oxybutylene group. It is particularly preferable that the polysiloxane-based macromonomer according to the invention has a polyoxypropylene chain having the oxypropylene group ($—CH(CH_3)CH_2O—$) as the repeating unit.

A number of repetition of the oxyalkylene group other than the oxyethylene group is appropriately selected depending on the kind of the oxyalkylene group constituting the polyoxyalkylene chain. For instance, in the case of the polyoxyalkylene chain having the oxypropylene group as the repeating unit, it is preferable that the number of repetition of the oxypropylene group is within a range from 5 to 16.

The polysiloxane-based macromonomer according to the invention is configured so as to have the polyoxyethylene chain and the polyoxyalkylene chain other than the polyoxyethylene chain, as described above, and such that the HLB value calculated according to the formula given below is held within the range from 0.7 to 6.0. The polysiloxane-based macromonomer according to the invention can exhibit good compatibility with respect to both of the hydrophobic monomer and the hydrophilic monomer, since the HLB value is held within the predetermined range. In this respect, it is noted the formula given below is widely used to calculate the HLB value ["Shin-ban Kaimen Kasseizai Handobukku (New Edition of Surfactant Handbook)" p. 234, edited by Yoshida Tokiyuki and three others, issued by Kougaku Tosho K.K.].

[HLB value]=$E/5$

In the above-indicated formula, E represents the weight fraction (wt %) of the oxyethylene group in the molecule of the polysiloxane-based macromonomer.

Further, excellent oxygen permeability is given to the ophthalmic lens obtained by using the polysiloxane-based macromonomer according to the invention, since the polysiloxane-based macromonomer according to the invention has, in its molecular chain, the polysiloxane chain having the siloxane unit as the repeating unit. Particularly in the case where the polysiloxane-based macromonomer according to the invention has a structure in which the polymerizable group is bonded through one or more urethane bond(s) to the polysiloxane chain constituting the main chain of the molecule of the macromonomer, the presence of the urethane bond(s) having a high degree of elasticity or resilience gives advantages that the ophthalmic lens obtained by using the polysiloxane-based macromonomer is reinforced without deterioration of its excellent oxygen permeability owing to the siloxane chain, and imparted with elastic resilience, whereby the ophthalmic lens becomes less fragile and has an improved mechanical strength.

As described above, the polysiloxane-based macromonomer for the ophthalmic lens according to the invention is configured so as to have the specific polyoxyethylene chain and the polyoxyalkylene chain other than the polyoxyethylene chain, and such that the HLB value calculated according to the above-indicated formula is held within the predetermined range. An example of the structure of the polysiloxane-based macromonomer is represented by a general formula (I) given below.

[Chemical Formula 1]

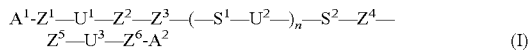

$$A^1-Z^1-U^1-Z^2-Z^3-(-S^1-U^2-)_n-S^2-Z^4-Z^5-U^3-Z^6-A^2 \quad (I)$$

In the above-indicated general formula (I), $A^1$ is a group represented by a general formula (II) given below, and $A^2$ is a group represented by a general formula (III) given below.

$$Y^{21}-R^{21}- \quad (II)$$

$$-R^{22}-Y^{22} \quad (III)$$

In the above-indicated general formulas (II) and (III), both of $Y^{21}$ and $Y^{22}$ are polymerizable groups, and each of $Y^{21}$ and $Y^{22}$ represents an acryloyloxy group, a methacryloyloxy group, a vinyl group or an allyl group, independently of each other. On the other hand, each of $R^{21}$ and $R^{22}$ represents a direct bond or a linear or branched alkylene group having 2 to 6 carbon atoms, independently of each other. The alkylene group is preferably an ethylene group, a propylene group or a butylene group.

In the above-indicated general formula (I), each of $Z^1$, $Z^2$, $Z^3$, $Z^4$, $Z^5$ and $Z^6$ represents a direct bond or a polyoxyalkylene chain having an oxyalkylene group as a repeating unit, independently of one another. At least one of $Z^1$ to $Z^6$ is the polyoxyethylene chain in which the number of repetition of the oxyethylene group is two or more, and at least one of $Z^1$ to $Z^6$ which is not the polyoxyethylene chain is the polyoxyalkylene chain having the oxyalkylene group other than the oxyethylene group as the repeating unit. As described above, the number of repetition of the oxyethylene group in the polyoxyethylene chain is preferably within the range from 4 to 15, and more preferably within the range from 4 to 10, and the polyoxyalkylene chain having the oxyalkylene group other than the oxyethylene group as the repeating unit is preferably the polyoxypropylene chain in which the number of repetition of the oxypropylene group is within the range from 5 to 16.

In the above-indicated general formula (I), $U^1$ is a group represented by a general formula (IV) given below, and includes the urethane bond in the molecular chain of the polysiloxane-based macromonomer.

$$-E^{21}-X^{21}- \quad (IV)$$

In the above-indicated general formula (IV), $E^{21}$ represents a —NHCO— group (in this case, $E^{21}$ forms the urethane bond with $X^{21}$) or a divalent group derived from a diisocyanate selected from a group consisting of saturated aliphatic diisocyanates, unsaturated aliphatic diisocyanates, alicyclic diisocyanates and aromatic diisocyanates (in this case, $E^{21}$ forms the urethane bond with each of $Z^1$ and $X^{21}$), and $X^{21}$ represents an oxygen atom.

In the above-indicated general formula (I), $U^2$ is a group represented by a general formula (VI) given below, and includes the urethane bond in the molecular chain of the polysiloxane-based macromonomer.

$$-R^{41}-X^{41}-E^{41}-X^{42}-R^{42}- \quad (VI)$$

In the above-indicated general formula (VI), each of $R^{41}$ and $R^{42}$ represents a linear or branched alkylene group having 2 to 6 carbon atoms, independently of each other, and each of $X^{41}$ and $X^{42}$ represents an oxygen atom or an alkylene glycol group, independently of each other, while $E^{41}$ represents a divalent group derived from a diisocyanate selected from the group consisting of saturated aliphatic diisocyanates, unsaturated aliphatic diisocyanates, alicyclic diisocyanates and aromatic diisocyanates (in this case, $E^{41}$ forms the urethane bond with each of $X^{41}$ and $X^{42}$).

In the above-indicated general formula (I), $U^3$ is a group represented by a general formula (VII) given below, and includes the urethane bond in the molecular chain of the polysiloxane-based macromonomer.

$$-X^{22}-E^{22}- \quad (VII)$$

In the above-indicated general formula (VII), $X^{22}$ represents an oxygen atom, and $E^{22}$ represents the —NHCO— group (in this case, $E^{22}$ forms the urethane bond with $X^{22}$) or a divalent group derived from a diisocyanate selected from the group consisting of saturated aliphatic diisocyanates, unsaturated aliphatic diisocyanates, alicyclic diisocyanates and aromatic diisocyanates (in this case, $E^{22}$ forms the urethane bond with each of $Z^5$ and $X^{22}$).

Examples of the divalent groups which are represented by $E^{21}$ in the above-indicated general formula (IV), $E^{41}$ in the above-indicated general formula (VI), and $E^{22}$ in the above-indicated general formula (VII), and which are derived from the diisocyanates selected from the group consisting of saturated aliphatic diisocyanates, unsaturated aliphatic diisocyanates, alicyclic diisocyanates and aromatic diisocyanates include: divalent groups derived from saturated aliphatic diisocyanates such as ethylene diisocyanate, propane-1,3-diisocyanate and hexamethylene diisocyanate; divalent groups derived from alicyclic diisocyanates such as cyclohexane-1,2-diisocyanate, bis(4-isocyanatecyclohexyl)methane and isophorone diisocyanate; divalent groups derived from aromatic diisocyanates such as tolylene diisocyanate and naphthalene-1,5-diisocyanate; and divalent groups derived from unsaturated aliphatic diisocyanates such as 2,2'-diisocyanate diethyl fumarate. Among the above-indicated divalent groups, the divalent groups respectively derived from hexamethylene diisocyanate and isophorone diisocyanate are advantageously employed in the present invention, since those divalent groups are relatively easily available and can impart a high degree of strength to the ophthalmic lens to be obtained as the end product.

In the above-indicated general formula (I), each of $S^1$ and $S^2$, which are independent of each other, is a group represented by a general formula (V) given below.

[Chemical Formula 2]

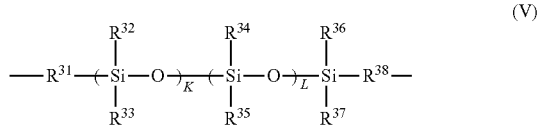

In the above-indicated general formula (V), each of $R^{31}$ and $R^{38}$ represents a linear or branched alkylene group having 2 to 6 carbon atoms, independently of each other, and each of $R^{32}$, $R^{33}$, $R^{34}$, $R^{35}$, $R^{36}$ and $R^{37}$ represents an alkyl group having 1 to 6 carbon atom(s), a fluorine-substituted alkyl group or a phenyl group, independently of one another.

Examples of the fluorine-substituted alkyl group described above include 3,3,3-trifluoro-n-propyl group, 2,2,2-trifluoroisopropyl group, 4,4,4-trifluoro-n-butyl group, 3,3,3-trifluoroisobutyl group, 3,3,3-trifluoro-sec-butyl group, 2,2,2-trifluoro-tert-butyl group, 5,5,5-trifluoro-n-pentyl group, 4,4,4-trifluoroisopentyl group, 3,3,3-trifluoro-neopentyl group and 6,6,6-trifluorohexyl group. An anti-stain property of the ophthalmic lens against deposition of protein, lipid or the like can be effectively improved by using the polysiloxane-based macromonomer having the above-indicated fluorine-substituted alkyl group, and increasing an amount of use of the macromonomer.

In the above-indicated general formula (V), K is an integer within a range from 1 to 1500, L is 0 or an integer within the range from 1 to 1500, and a sum of K and L:

"K+L" is an integer within the range from 1 to 1500. Where the value "K+L" is larger than 1500, the polysiloxane-based macromonomer has an excessively large molecular weight, whereby compatibility of the macromonomer with the other polymerizable components to be mixed with the macromonomer in the production of the ophthalmic lens is deteriorated, giving rise to a risk that the macromonomer cannot be sufficiently dissolved at the time of its mixing with the other components, or the mixture is clouded at the time of polymerization, resulting in failure to obtain a homogeneous and transparent material for the ophthalmic lens. On the other hand, the value "K+L" of 0 not only results in reduction of the oxygen permeability of the ophthalmic lens material obtained by using the macromonomer, but also results in tendency of reduction of flexibility of the ophthalmic lens material. In the polysiloxane-based macromonomer according to the invention, the value "K+L" is preferably an integer within a range from 2 to 1000, and more preferably an integer within a range from 3 to 500.

In the above-indicated general formula (I), n is 0 or an integer within a range from 1 to 10. Where the value n is larger than 10, the polysiloxane-based macromonomer has an excessively large molecular weight, whereby compatibility of the macromonomer with the other polymerizable components to be mixed with the macromonomer in the production of the ophthalmic lens is deteriorated, giving rise to the risk that the macromonomer cannot be sufficiently dissolved at the time of its mixing with the other components, or the mixture is clouded at the time of polymerization, resulting in the failure to obtain a homogeneous and transparent material for the ophthalmic lens. The value n in the above-indicated general formula (I) is more preferably 0 or an integer within a range from 1 to 5.

Preferable forms of the polysiloxane-based macromonomer for the ophthalmic lens according to the invention are represented by general formulas (VIII) and (IX) given below, for example. However, it goes without saying that the polysiloxane-based macromonomer according to the invention is not limited to those represented by the general formulas (VIII) and (IX).

[Chemical Formula 3]

General formula (VIII)

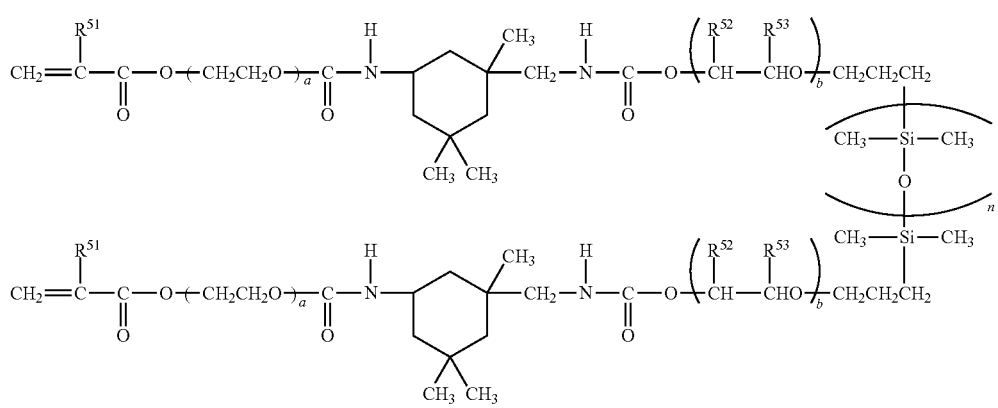

(In the above-indicated general formula (VIII), $R^{51}$ represents a hydrogen atom or a methyl group, a is an integer not smaller than two, b is an integer not smaller than two and n is an integer within a range from 1 to 1500. Further, each of $R^{52}$ and $R^{53}$ is a hydrogen atom or a methyl group, wherein $R^{53}$ is the methyl group in the case where $R^{52}$ is the hydrogen atom, and $R^{53}$ is the hydrogen atom in the case where $R^{52}$ is the methyl group.)

[Chemical Formula 4]

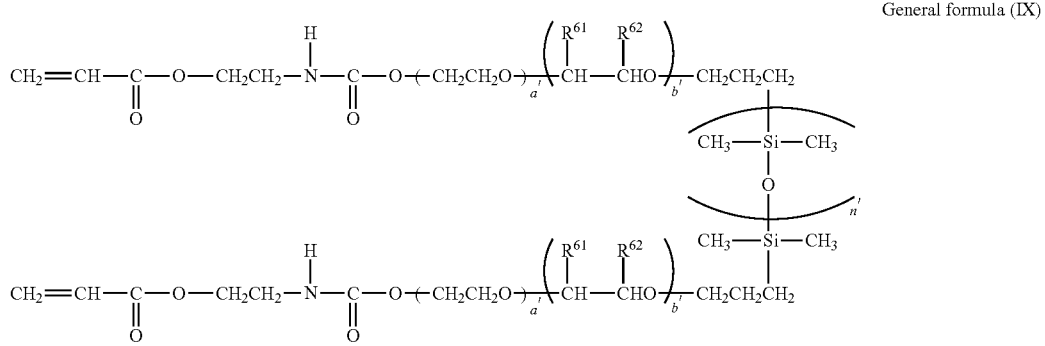

General formula (IX)

(In the above-indicated general formula (IX), a' is an integer not smaller than two, b' is an integer not smaller than two and n' is an integer within a range from 1 to 1500. Further, each of $R^{61}$ and $R^{62}$ is a hydrogen atom or a methyl group, wherein $R^{62}$ is the methyl group in the case where $R^{61}$ is the hydrogen atom, and $R^{62}$ is the hydrogen atom in the case where $R^{61}$ is the methyl group.)

By the way, the polysiloxane-based macromonomer for the ophthalmic lens according to the invention can be produced by using various known compounds as starting materials (raw materials), and successively or stepwisely reacting those compounds with each other by a conventional method.

For instance, the polysiloxane-based macromonomer represented by the above-indicated general formula (VIII) can be advantageously produced by conducting a two-step urethanization reaction. Specifically, a compound having isocyanate groups (or hydroxy groups) at both of its ends is initially synthesized by reacting a polysiloxane compound which is modified with polypropylene oxide at both of its terminals, with a diisocyanate compound, by using a predetermined solvent and/or catalyst, as necessary (urethanization reaction I).

Regarding the polysiloxane compound which is modified with polypropylene oxide at both of its terminals and which is subjected to the urethanization reaction I, it is noted that a number of repetition of propylene oxide (oxypropylen group) in polypropylene oxide portions, and a number of repetition of a siloxane bond in a polysiloxane portion, are appropriately determined depending on the structure of the intended polysiloxane-based macromonomer. On the other hand, examples of the diisocyanate compound include isophorone diisocyanate, ethylene diisocyanate, 1,6-hexamethylene diisocyanate, 1,2-toluene diisocyanate, 1,4-toluene diisocyanate, xylylene diisocyanate, bis(2-isocyanatoethyl) fumarate, 1,5-naphthalene diisocyanate, cyclohexyl-1,4-diisocyanate, 4,4'-dicyclohexyl methane diisocyanate, diphenylmethane-4,4'-diisocyanate, and 2,2,4-(2,4,4)-trimethylhexane-1,6-diisocyanate.

Then, the compound which has the isocyanate group (or hydroxy group) at its both ends, and which is obtained by the urethanization reaction I, is reacted with polyethylene glycol monomethacrylate, by using a predetermined solvent and/or catalyst, as necessary (urethanization reaction II), and a known purification operation is performed on the thus obtained reaction product, whereby the intended polysiloxane-based macromonomer is obtained.

On the other hand, the polysiloxane-based macromonomer represented by the above-indicated general formula (IX) is produced by initially reacting a dimethylpolysiloxane compound having SiH groups at both of its terminals, with a propyleneoxide-ethyleneoxide compound having an allyl group at its terminal, by using a predetermined solvent and/or catalyst, as necessary, whereby a polysiloxane compound having polyether at both of its terminals is synthesized.

Then, the polysiloxane compound having polyether at both of its terminals is reacted with an isocyanate compound, and a known purification operation is performed on the thus obtained reaction product, whereby the intended polysiloxane-based macromonomer is obtained.

It is noted that the starting materials (raw materials) indicated with respect to each of the production processes described above are merely examples of the starting materials. It is possible to use any starting material (raw material) which permits production of the polysiloxane-based macromonomer for the ophthalmic lens according to the invention. Further, it goes without saying that the polysiloxane-based macromonomer for the ophthalmic lens according to the invention can be produced by a process other than those described above.

The thus obtained polysiloxane-based macromonomer according to the invention is configured so as to have the specific polyoxyethylene chain and the polyoxyalkylene chain other than the polyoxyethylene chain, and such that the HLB value calculated according to the predetermined formula is held within the predetermined range, whereby the polysiloxane-based macromonomer can exhibit good compatibility with respect to both of the hydrophobic monomer and the hydrophilic monomer, which have been generally used in the production of the ophthalmic lens. Therefore, the polysiloxane-based macromonomer for the ophthalmic lens according to the invention can be used in combination with the other components, which combination has been difficult to employ for the conventional polysiloxane-based macromonomer due to compatibility with the other components (particularly with the hydrophilic monomer), to permit production of the ophthalmic lens having more excellent properties than the conventional ophthalmic lens.

By the way, in production of the contact lens as a kind of the ophthalmic lens by using the polysiloxane-based macromonomer for the ophthalmic lens according to the invention, a polymerizable composition including the polysiloxane-based macromonomer according to the invention is initially prepared. In the preparation of the polymerizable composition, there are used various components appropriately selected from those conventionally used in the production of the contact lens depending on the type of the contact lens to be obtained.

For instance, in order to produce the contact lens, the polymerizable composition is prepared by using the hydrophilic monomer and the hydrophobic monomer, as well as the polysiloxane-based macromonomer according to the invention, and further using a crosslinking agent, a reinforcing agent, a hydrophilicity agent, an ultraviolet-absorbing agent, a colorant or the like, as necessary. Each of the above-indicated components may be selected from various compounds conventionally used in the production of the contact lens.

Specific examples of the hydrophilic monomer include: N-vinylpyrrolidone (NVP); acrylamide-based monomers such as acrylamide, N, N-dimethylacrylamide (DMAA), N,N-diethylacrylamide, N,N-dimethylaminopropylacrylamide, N-isopropylacrylamide and acryloylmorpholine; hydroxyalkyl acrylates such as 2-hydroxyethyl acrylate, hydroxypropyl acrylate and hydroxybutyl acrylate; (alkyl) aminoalkyl acrylates such as 2-dimethylaminoethyl acrylate and 2-butylaminoethyl acrylate; alkylene glycol monoacrylates such as ethylene glycol monoacrylate and propylene glycol monoacrylate; ethylene glycol allyl ether; ethylene glycol vinyl ether; acrylic acid; aminostyrene; hydroxystyrene; vinyl acetate; glycidyl acrylate; allylglycidylether; vinyl propionate; N-vinyl lactams such as N-vinyl-3-methyl-2-pyrrolidone, N-vinyl-4-methyl-2-pyrrolidone, N-vinyl-5-methyl-2-pyrrolidone, N-vinyl-6-methyl-2-pyrrolidone, N-vinyl-3-ethyl-2-pyrrolidone, N-vinyl-4,5-dimethyl-2-pyrrolidone, N-vinyl-5,5-dimethyl-2-pyrrolidone, N-vinyl-3,3,5-trimethyl-2-pyrrolidone, N-vinyl-2-piperidone, N-vinyl-3-methyl-2-piperidone, N-vinyl-4-methyl-2-piperidone, N-vinyl-5-methyl-2-piperidone, N-vinyl-6-methyl-2-piperidone, N-vinyl-6-ethyl-2-piperidone, N-vinyl-3,5-dimethyl-2-piperidone, N-vinyl-4,4-dimethyl-2-piperidone, N-vinyl-2-caprolactam, N-vinyl-7-methyl-2-caprolactam, N-vinyl-7-ethyl-2-caprolactam, N-vinyl-3,5-dimethyl-2-caprolactam, N-vinyl-4,6-dimethyl-2-caprolactam and N-vinyl-3,5,7-trimethyl-2-caprolactam; N-vinylamides such as N-vinylformamide, N-vinyl-N-methylformamide, N-vinyl-N-ethylformamide, N-vinylacetamide, N-vinyl-N-methylacetamide, N-vinyl-N-ethylacetamide and N-vinylphthalimide; and 1-methyl-3-methylene-2-pyrrolidinone.

As the hydrophobic monomer, it is possible to use, for example, a silicon-containing monomer and a fluorine-containing alkyl (meth)acrylate, which are conventionally used for the ophthalmic lens material. These hydrophobic monomers are used as auxiliary components for the polysiloxane-based macromonomer according to the invention. It is particularly noted that compatibility of the polymerizable composition can be improved by addition of the silicon-containing monomer other than the polysiloxane-based macromonomer according to the invention, since the silicon-containing monomer has a lower molecular weight than the polysiloxane-based macromonomer according to the invention. On the other hand, the fluorine-containing alkyl (meth) acrylate improves solubility of oxygen into the lens (polymer), which solubility is one of factors that influence the oxygen permeability of the contact lens. Further, the fluorine-containing alkyl (meth)acrylate reduces adhesiveness (tackiness) of lens surfaces, and effectively prevents adhesion of lipid or the like to the lens surfaces, owing to its hydrophobic and lipophobic properties, to improve the antistain property of the lens. It is to be understood that the expression " . . . (meth)acrylate" is used in this specification as a generic expression including " . . . acrylate" and " . . . methacrylate".

Examples of the silicon-containing monomer described above include generally used silicon-containing monomers such as siloxanyl (meth)acrylate and siloxanyl styrene wherein a pentamethyl disiloxymethyl group, a bis(trimethylsiloxy) (methyl)silylmethyl group, a bis(trimethylsiloxy) (methyl)silylpropyl group, a tris(trimethylsiloxy) silylmethyl group, a tris(trimethylsiloxy) silylpropyl group or the like is introduced into (meth)acrylate, styrene or the like. Among the above-indicated silicon-containing monomers, bis(trimethylsiloxy) (methyl)silylpropyl (meth)acrylate and tris(trimethylsiloxy) silylpropyl (meth)acrylate are particularly preferably used in view of ease of purification, oxygen permeability, availability, compatibility, etc.

Examples of the fluorine-containing alkyl (meth)acrylate include 2,2,2-trifluoroethyl (meth)acrylate, 2,2,3,3,3-pentafluoropropyl (meth)acrylate, (perfluorobutyl)ethyl (meth) acrylate, (perfluorohexyl)ethyl (meth)acrylate, (perfluorooctyl)ethyl (meth)acrylate, (perfluorodecyl)ethyl (meth) acrylate and (perfluorododecyl)ethyl (meth)acrylate. Among the above-indicated fluorine-containing alkyl (meth)acrylates, one having a fluorinated portion of a large molecular weight is more preferably employed, since such a fluorine-containing alkyl (meth)acrylate is suitable to achieve more excellent oxygen permeability, and gives an adequate degree of flexibility or softness to the lens. Examples of the fluorine-containing alkyl (meth)acrylate having the fluorinated portion of a large molecular weight include (perfluorohexyl)ethyl (meth)acrylate, (perfluorooctyl)ethyl (meth) acrylate and (perfluorodecyl)ethyl (meth)acrylate. Among the above-indicated fluorine-containing alkyl (meth)acrylates, (perfluorooctyl)ethyl (meth)acrylate is most preferable, since it is commercially available and can be easily purified by distillation under a reduced pressure, for example.

On the other hand, the crosslinking agent is used as necessary in order to improve the mechanical strength of the contact lens and to make the contact lens maintain its shape with a higher degree of stability, for example. The crosslinking agent is appropriately used depending on the kind of the polysiloxane-based macromonomer according to the invention. For instance, in the case where the polysiloxane-based macromonomer according to the invention has a multiplicity of polymerizable groups in a molecule, use of the crosslinking agent is not usually required. On the other hand, in the case where the number of the polymerizable group in the polysiloxane-based macromonomer according to the invention is relatively small, and in the case where an amount of use of the above-indicated hydrophobic monomer is relatively small, there is a risk that the contact lens has problems in terms of its shape stability, strength, durability, for example, so that it is preferable to use a suitable crosslinking agent.

It is possible to use any of various known crosslinking agents which have at least two polymerizable groups and which are conventionally used for the ophthalmic lens material. Examples of the crosslinking agent include: (meth) acrylates of polyhydric alcohols such as ethylene glycol, diethylene glycol, triethylene glycol, propylene glycol, 1,4-butanediol, 1,6-hexanediol, trimethylol propane and pentaerythritol; divinyl adipate; diallyl adipate; allyl ester vinyl ester adipate; divinyl sebacate; diallyl sebacate; allyl ester vinyl ester sebacate; vinyl esters and allyl esters of polybasic carboxylic acids such as oxalic acid, malonic acid, maleic acid, methylmalonic acid, succinic acid, dimethylmalonic acid, ethylmalonic acid, methylsuccinic acid, glutaric acid, dimethylsuccinic acid, isopropylmalonic acid, methylglutaric acid, methyladipic acid, pimelic acid, suberic acid, di-n-propylmalonic acid, 1,9-nonanedicarboxylic acid, 1,10-decanedicarboxylic acid, 1,3-phenylenediacetic acid, phenylsuccinic acid, benzylmalonic acid, 1,2,3-propanetricarboxylic acid, 1,3,5-pentanetricarboxylic acid and 1,2,3,4-butanetetracarboxylic acid. In view of the solubility, it is more preferable that all carboxyl groups in each of the polybasic carboxylic acids described above are esterified (completely esterified). Examples of the crosslinking agent further include: divinyl benzene; triallyl cyanurate; triallyl isocyanurate; diethylene glycol bisallyl carbonate; triallyl ester of trimellitic acid; allyl ether; diallyl ether of alkylene glycol or polyalkylene glycol; divinyl ether of alkylene glycol or polyalkylene glycol; allyl ether vinyl ether of alkylene glycol or polyalkylene glycol; diallylidene pentaerythritol; 1,3,5-trivinyl-1,3,5-trimethylcyclotrisiloxane; vinyl (meth)acrylate; and allyl (meth)acrylate. At least one of the above-indicated known crosslinking agents is suitably selected and used.

The crosslinking agent is preferably used in the polymerizable composition in an amount of 0.0005-10 parts by weight per 100 parts by weight of a total amount of the monomer components (polysiloxane-based macromonomer according to the invention, hydrophilic monomer and hydrophobic monomer) described above. In the case where the crosslinking agent is required and the amount of its use is excessively small, the effect of the crosslinking agent cannot be sufficiently achieved, giving rise to a risk that the contact lens which has absorbed water fails to keep its shape such as a circular shape with high stability, and to have an adequate degree of elasticity, for example. On the other hand, an excessively large amount of use of the crosslinking agent results in an excessively large number of crosslinking points in a polymer, giving rise to a risk that the contact lens becomes fragile and is easily broken.

The reinforcing agent is used for adjusting the mechanical strength of the contact lens. For instance, in the case where the polysiloxane-based macromonomer according to the invention has a multiplicity of polymerizable groups in a molecule, the polysiloxane-based macromonomer itself has a crosslinking effect, so that the contact lens having excellent resilience can be obtained by using the macromonomer. However, in the case where the strength of the contact lens is lowered due to the crosslinking effect of the polysiloxane-based macromonomer, it is preferable to use the reinforcing agent.

It is possible to use any of various known reinforcing agents conventionally used for the ophthalmic lens material. Specific examples of the reinforcing agent include: vinyl esters and allyl esters of organic carboxylic acids such as vinyl acetate and allyl propionate; (meth)acrylate and its macromonomer; and styrene derivatives. At least one of the above-indicated known reinforcing agents is suitably selected and used.

The reinforcing agent is preferably used in the polymerizable composition in an amount of 1-20 parts by weight per 100 parts by weight of the total amount of the monomer components (polysiloxane-based macromonomer according to the invention, hydrophilic monomer and hydrophobic monomer) described above. In the case where the reinforcing agent is used in an amount less than 1 part by weight per 100 parts by weight of the monomer components, there is a risk of failure to sufficiently achieve a reinforcing effect. On the other hand, in the case where more than 20 parts by weight of the reinforcing agent is used per 100 parts by weight of the monomer components, it is difficult to achieve a desired degree of oxygen permeability of the contact lens, and there is a risk that the contact lens cannot have a sufficiently high water content.

The hydrophilicity agent is used for giving hydrophilicity to the contact lens. It is preferable to appropriately use the hydrophilicity agent in the case where the contact lens obtained by copolymerization of the polymerizable composition including the above-described monomer components has the intended water content, but the surfaces of the contact lens do not exhibit sufficiently high hydrophilicity or wettability. The hydrophilicity agent is also preferably used in each of the cases where compatibility of polymerizable monomers with respect to each other is insufficient, the contact lens has excessively high elasticity, and the polymerizable composition has extremely high affinity with respect to materials of vessels used for polymerization of the polymerizable composition and/or formation of the contact lens.

It is possible to use any known hydrophilicity agent conventionally used for the ophthalmic lens material. Examples of the hydrophilicity agent include: mono(meth)acrylates of polyhydric alcohols such as ethylene glycol, propylene glycol and 1,6-hexane diol; N-(meth)acryloyl morpholine; N-(meth)acryloyl piperidine; N-vinyl piperidone; N-vinyl-N-methyl acetamide; N-vinyl-N-ethyl acetamide; N-vinyl-N-methyl formamide; and N-methyl-α-methylene-2-pyrrolidone. At least one of the above-indicated known hydrophilicity agents is suitably selected and used.

The hydrophilicity agent is used in the polymerizable composition in an amount of 1-30 parts by weight per 100 parts by weight of the total amount of the monomer components (polysiloxane-based macromonomer according to the invention, hydrophilic monomer and hydrophobic monomer) described above. In the case where the hydrophilicity agent is required and used in an amount less than 1 part by weight per 100 parts by weight of the monomer components, there is a risk that the hydrophilicity agent cannot sufficiently exhibit its hydrophilization effect on the contact lens to be obtained as the end product. On the other hand, in the case where more than 30 parts by weight of the hydrophilicity agent is used per 100 parts by weight of the monomer components, there is a risk of deterioration of compatibility of the monomers with respect to each other, and difficulty in achieving the desired degree of oxygen permeability.

In the production of the contact lens by using the polysiloxane-based macromonomer according to the invention, it is also possible to use various other components or additives which are generally used in the production of the contact lens, as necessary, in addition to the components described above. Examples of the other components or additives include: a polymerizable ultraviolet-absorbing agent for imparting ultraviolet absorptivity to the contact lens; a polymerizable colorant for coloring the contact lens; and a polymerizable ultraviolet-absorbing colorant for imparting the ultraviolet absorptivity to the contact lens and coloring the contact lens.

Examples of the polymerizable ultraviolet-absorbing agent include: benzophenone-based polymerizable ultraviolet-absorbing agents such as 2-hydroxy-4-(meth)acryloyloxybenzophenone, 2-hydroxy-4-(meth)acryloyloxy-5-tert-butylbenzophenone, 2-hydroxy-4-(meth)acryloyloxy-2',4'-dichlorobenzophenone and 2-hydroxy-4-(2'-hydroxy-3'-(meth)acryloyloxypropoxy)benzophenone; benzotriazole-based polymerizable ultraviolet-absorbing agents such as 2-(2'-hydroxy-5'-(meth)acryloyloxyethylphenyl)-2H-benzotriazole [HMEPBT], 2-(2'-hydroxy-5'-(meth)acryloyloxyethylphenyl)-5-chloro-2H-benzotriazole, 2-(2'-hydroxy-5'-(meth)acryloyloxypropylphenyl)-2H-benzotriazole, 2-(2'-hydroxy-5'-(meth)acryloyloxypropyl-3'-tert-butylphenyl)-5-chloro-2H-benzotriazole and 2-(2'-hydroxy-5'-(2"-methacryloyloxyethoxy)-3'-tert-butylphenyl)-5-methyl-2H-benzotriazole; salicylic acid derivative-based polymerizable ultraviolet-absorbing agents such as phenyl 2-hydroxy-4-(meth)acryloyloxymethylbenzoate; and methyl 2-cyano-3-phenyl-3-(3'-(meth)acryloyloxyphenyl)propenoate. The above-indicated polymerizable ultraviolet-absorbing agents may be used alone or in combination as a mixture of two or more of them.

Examples of the polymerizable colorant include azo-based polymerizable colorants such as 1-phenylazo-4-(meth)acryloyloxynaphthalene, 1-phenylazo-2-hydroxy-3-(meth)acryloyloxynaphthalene, 1-naphthylazo-2-hydroxy-3-(meth)acryloyloxynaphthalene, 1-($\alpha$-anthrylazo)-2-hydroxy-3-(meth)acryloyloxynaphthalene, 1-((4'-(phenylazo)-phenyl)azo)-2-hydroxy-3-(meth)acryloyloxynaphthalene, 1-(2',4'-xylylazo)-2-(meth)acryloyloxynaphthalene, 1-(o-tolylazo)-2-(meth)acryloyloxynaphthalene, 2-(m-(meth)acryloylamide-anilino)-4,6-bis(1'-(o-tolylazo)-2'-naphthylamino)-1,3,5-triazine, 2-(m-vinylanilino)-4-((4'-nitrophenylazo)-anilino)-6-chloro-1,3,5-triazine, 2-(1'-(o-tolylazo)-2'-naphthyloxy)-4-(m-vinylanilino)-6-chloro-1,3,5-triazine, 2-(p-vinylanilino)-4-(1'-(o-tolylazo)-2'-naphthylamino)-6-chloro-1,3,5-triazine, N-(1'-(o-tolylazo)-2'-naphthyl)-3-vinylphthalic acid monoamide, N-(1'-(o-tolylazo)-2'-naphthyl)-6-vinylphthalic acid monoamide, 3-vinylphthalic acid-(4'-(p-sulfophenylazo)-1'-naphthyl)monoester, 6-vinylphthalic acid-(4'-(p-sulfophenylazo)-1'-naphthyl)monoester, 3-(meth)acryloylamide-4-phenylazophenol, 3-(meth)acryloylamide-4-(8'-hydroxy-3',6'-disulfo-1'-naphthylazo)phenol, 3-(meth)acryloylamide-4-(1'-phenylazo-2'-naphthylazo)phenol, 3-(meth)acryloylamide-4-(p-tolylazo)phenol, 2-amino-4-(m-(2'-hydroxy-1'-naphthylazo)anilino)-6-isopropenyl-1,3,5-triazine, 2-amino-4-(N-methyl-p-(2'-hydroxy-1'-naphthylazo)anilino)-6-isopropenyl-1,3,5-triazine, 2-amino-4-(m-(4'-hydroxy-t-phenylazo)anilino)-6-isopropenyl-1,3,5-triazine, 2-amino-4-(N-methyl-p-(4'-hydroxyphenylazo)anilino)-6-isopropenyl-1,3,5-triazine, 2-amino-4-(m-(3'-methyl-1'-phenyl-5'-hydroxy-4'-pyrazolylazo)anilino)-6-isopropenyl-1,3,5-triazine, 2-amino-4-(N-methyl-p-(3'-methyl-1'-phenyl-5'-hydroxy-4'-pyrazolylazo)anilino)-6-isopropenyl-1,3,5-triazine, 2-amino-4-(p-phenylazoanilino)-6-isopropenyl-1,3,5-triazine and 4-phenylazo-7-(meth)acryloylamide-1-naphthol.

Further examples of the polymerizable colorant include: anthraquinone-based polymerizable colorants such as 1,5-bis((meth)acryloylamino)-9,10-anthraquinone, 1-(4'-vinylbenzoylamide)-9,10-anthraquinone, 4-amino-1-(4'-vinylbenzoylamide)-9,10-anthraquinone, 5-amino-1-(4'-vinylbenzoylamide)-9,10-anthraquinone, 8-amino-1-(4'-vinylbenzoylamide)-9,10-anthraquinone, 4-nitro-1-(4'-vinylbenzoylamide)-9,10-anthraquinone, 4-hydroxy-1-(4'-vinylbenzoylamide)-9,10-anthraquinone, 1-(3'-vinylbenzoylamide)-9,10-anthraquinone, 1-(2'-vinylbenzoylamide)-9,10-anthraquinone, 1-(4'-isopropenylbenzoylamide)-9,10-anthraquinone, 1-(3'-isopropenylbenzoylamide)-9,10-anthraquinone, 1-(2'-isopropenylbenzoylamide)-9,10-anthraquinone, 1,4-bis-(4'-vinylbenzoylamide)-9,10-anthraquinone, 1,4-bis-(4'-isopropenylbenzoylamide)-9,10-anthraquinone, 1,5'-bis-(4'-vinylbenzoylamide)-9,10-anthraquinone, 1,5-bis-(4'-isopropenylbenzoylamide)-9,10-anthraquinone, 1-methylamino-4-(3'-vinylbenzoylamide)-9,10-anthraquinone, 1-methylamino-4-(4'-vinylbenzoyloxyethylamino)-9,10-anthraquinone, 1-amino-4-(3'-vinylphenylamino)-9,10-anthraquinone-2-sulfonic acid, 1-amino-4-(4'-vinylphenylamino)-9,10-anthraquinone-2-sulfonic acid, 1-amino-4-(2'-vinylbenzylamino)-9,10-anthraquinone-2-sulfonic acid, 1-amino-4-(3'-(meth)acryloylaminophenylamino)-9,10-anthraquinone-2-sulfonic acid, 1-amino-4-(3'-(meth)acryloylaminobenzylamino)-9,10-anthraquinone-2-sulfonic acid, 1-($\beta$-ethoxycarbonylallylamino)-9,10-anthraquinone, 1-($\beta$-carboxyallylamino)-9,10-anthraquinone, 1,5-di-($\beta$-carboxyallylamino)-9,10-anthraquinone, 1-($\beta$-isopropoxycarbonylallylamino)-5-benzoylamide-9,10-anthraquinone, 2-(3'-(meth)acryloylamide-anilino)-4-(3'-(3"-sulfo-4"-aminoanthraquinone-1"-yl)amino-anilino)-6-chloro-1,3,5-triazine, 2-(3'-(meth)acryloylamide-anilino)-4-(3'-(3"-sulfo-4"-aminoanthraquinone-1"-yl)amino-anilino)-6-hydrazino-1,3,5-triazine, 2,4-bis-((4"-methoxyanthraquinone-1"-yl)amino)-6-(3'-vinylanilino)-1,3,5-triazine and 2-(2'-vinylphenoxy)-4-(4'-(3"-sulfo-4"-aminoanthraquinone-1"-yl-amino)anilino)-6-chloro-1,3,5-triazine; nitro-based polymerizable colorants such as o-nitroanilinomethyl (meth) acrylate; and phthalocyanine-based polymerizable colorants such as (meth)acryloyl-modified tetraamino copper phthalocyanine and (meth)acryloyl-modified (dodecanoyl-modified tetraamino copper phthalocyanine). The above-indicated polymerizable colorants may be used alone or in combination as a mixture of two or more of them.

Examples of the polymerizable ultraviolet-absorbing colorant include benzophenone-based polymerizable ultraviolet-absorbing colorants such as 2,4-dihydroxy-3-(p-styrenoazo)benzophenone, 2,4-dihydroxy-5-(p-styrenoazo)benzophenone, 2,4-dihydroxy-3-(p-(meth) acryloyloxymethylphenylazo)benzophenone, 2,4-dihydroxy-5-(p-(meth)acryloyloxymethylphenylazo)benzophenone, 2,4-dihydroxy-3-(p-(meth)acryloyloxyethylphenylazo)benzophenone, 2,4-dihydroxy-5-(p-(meth)acryloyloxyethylphenylazo)benzophenone, 2,4-dihydroxy-3-(p-(meth)acryloyloxypropylphenylazo)benzophenone, 2,4-dihydroxy-5-(p-(meth)acryloyloxypropylphenylazo)benzophenone, 2,4-dihydroxy-3-(o-(meth)acryloyloxymethylphenylazo)benzophenone, 2,4-dihydroxy-5-(o-(meth)acryloyloxymethylphenylazo)benzophenone, 2,4-dihydroxy-3-(o-(meth)acryloyloxyethylphenylazo)benzophenone, 2,4-dihydroxy-5-(o-(meth)acryloyloxyethylphenylazo)benzophenone, 2,4-dihydroxy-5-(o-(meth)acryloyloxypropylphenylazo)benzophenone, 2,4-dihydroxy-3-(p-(N,N-di(meth)acryloyloxyethylamino)phenylazo)benzophenone, 2,4-dihydroxy-5-(p-(N,N-di(meth)acryloyloxyethylamino)phenylazo)benzophenone, 2,4-dihydroxy-3-(o-(N,N-di(meth)acryloyloxyethylamino)phenylazo)benzophenone, 2,4-dihydroxy-5-(o-(N,N-di(meth)acryloylethylamino)phenylazo)benzophenone, 2,4-dihydroxy-3-(p-(N-ethyl-N-(meth)acryloyloxyethylamino)phenylazo)benzophenone, 2,4-dihydroxy-5-(p-(N-ethyl-N-(meth)acryloyloxyethylamino)phenylazo)benzophenone, 2,4-dihydroxy-3-(o-(N-ethyl-N-(meth)acryloyloxyethylamino)phenylazo)benzophenone, 2,4-dihydroxy-5-(o-(N-ethyl-N-(meth)acryloyloxyethylamino)phenylazo)benzophenone, 2,4-dihydroxy-3-(p-(N-ethyl-N-(meth)acryloylamino)phenylazo)benzophenone, 2,4-dihydroxy-5-(p-(N-ethyl-N-(meth)acryloylamino)phenylazo)benzophenone, 2,4-dihydroxy-3-(o-(N-ethyl-N-(meth)acryloylamino)phenylazo)benzophenone, 2,4-dihydroxy-5-(o-(N-ethyl-N-(meth)acryloylamino)phenylazo)

benzophenone and 2,4-dihydroxy-5-(4-(2-(N-(2-methacryloyloxyethyl)carbamoyloxy)ethyl)phenylazo)benzo phenone; and benzoic acid-based polymerizable ultraviolet-absorbing colorants such as phenyl 2-hydroxy-4-(p-styrenoazo)benzoate. The above-indicated polymerizable ultraviolet-absorbing colorants may be used alone or in combination as a mixture of two or more of them.

The polymerizable ultraviolet-absorbing agent, the polymerizable colorant and the polymerizable ultraviolet-absorbing colorant are used in the polymerizable composition preferably in an amount not more than 3 parts by weight, and more preferably in an amount of 0.01-2 parts by weight, per 100 parts by weight of the total amount of the monomer components (polysiloxane-based macromonomer according to the invention, hydrophilic monomer and hydrophobic monomer) described above. In the case where more than 3 parts by mass of the polymerizable ultraviolet-absorbing agent and the like are used per 100 parts by weight of the monomer components, the mechanical strength of the contact lens to be obtained tends to be deteriorated, for example. Further, a smaller amount of use of the polymerizable ultraviolet-absorbing agent and the like is preferred taking account of tonicity of the ultraviolet-absorbing agent and the colorant.

In production of a water-absorptive contact lens by using the components described above, proportions of the respective components in the polymerizable composition are preferably determined such that the water content of the contact lens to be obtained as the end product is held within a range of 10-60%. In the case where the water content of the contact lens is less than 10%, the contact lens is pressed onto a cornea upon blinking of the eye, even in the presence of a tear fluid layer between the lens and the cornea, resulting in a decrease of a space between the lens and the cornea, and giving rise to a risk that the lens finally adheres or sticks to the cornea, like a sucker. On the other hand, in the case where the water content of the contact lens is more than 60%, there is a risk of reduction of the oxygen permeability. The proportions of the respective components in the polymerizable composition are particularly preferably determined such that the water content of the contact lens is held within a range of 12-55%.

The water content of the contact lens described in this specification is calculated as follows. Namely, after immersing the contact lens in water at 20° C. for two hours, the water remaining on the lens surfaces is wiped off with hygroscopic paper, and the weight ($W_1$) of the lens in its hydrated state is measured. Then, the contact lens is dried by leaving it in a drier at 60° C. for 24 hours, and the weight ($W_2$) of the thus dried contact lens is measured. By using the weight: $W_1$ of the lens in its hydrated state and the weight: $W_2$ of the lens in its dry state, the water content of the lens is calculated according to the following formula:

Water content(wt %)=[($W_1-W_2$)/$W_1$]×100

In order to produce, for example, the water-absorptive contact lens by using the thus prepared polymerizable composition including the components described above, the polymerizable composition is copolymerized by one of various known polymerization method.

More specifically described, examples of the polymerization method for polymerizing the polymerizable composition include: a method (heat polymerization method) in which a heat polymerization initiator is added to the polymerizable composition, and then the polymerizable composition is gradually or stepwisely heated within a range from the room temperature to about 150° C. for polymerization; a method (photopolymerization method) in which a photopolymerization initiator (and photosensitizer) is added to the polymerizable composition, and then the polymerizable composition is irradiated with a suitable ray of light (ultraviolet ray, electron beam or the like) for polymerization; and a combination of the heat polymerization method and the photopolymerization method. The polymerization may be conducted by a bulk polymerization process, a solution polymerization process or any other known polymerization process.

A method of forming (processing) the contact lens (ophthalmic lens) is not particularly limited. It is possible to employ any of various conventional methods known to those skilled in the art, such as: a mechanical processing method in which the polymerizable composition is accommodated and polymerized in a suitable polymerization mold or polymerization vessel, to obtain a contact lens material (ophthalmic lens material) in the form of a bar, a block, a plate or the like, which is formed of the polymer of the polymerizable composition, and then the contact lens material is formed into a desired shape by a machining process such as cutting, grinding or the like; a cast molding method (molding method) in which a predetermined polymerizable monomer composition is accommodated in a molding cavity of a polymerization mold which gives the shape of the intended contact lens, and a formed article is obtained by polymerizing the above-described polymerizable components within the polymerization mold; and a combination of the molding method and the mechanical processing method, in which a mechanical finishing process is performed as necessary. Among the above-described methods, the molding method is particularly preferably used to effectively reduce the cost of production of the lens.

Examples of the heat polymerization initiator which is used in the case where the polymerizable composition is polymerized by the heat polymerization method include 2,2'-azobisisobutyronitrile, 2,2'-azobis(2,4-dimethylvaleronitrile), benzoylperoxide, tert-butyl hydroperoxide, cumene hydroperoxide, lauroyl peroxide, tert-butylperoxy hexanoate and 3,5,5-trimethylhexanoylperoxide. The above-indicated heat polymerization initiators may be used alone or in combination as a mixture of two or more of them. The heat polymerization initiator is used preferably in an amount of 0.001-2 parts by weight, and more preferably in an amount of 0.01-1 part by weight, per 100 parts by weight of the total amount of the monomer components in the polymerizable composition described above.

In the heat polymerization method, the polymerizable composition is heated to a temperature preferably within a range of 50-150° C., and more preferably within a range of 60-140° C., for a time period of preferably 10-120 min, and more preferably 20-60 min. It is possible to reduce a required time for the polymerization by heating the polymerizable composition to a temperature not lower than 50° C. It is possible to reduce an amount of residual monomer component by heating the polymerizable composition for not shorter than 10 min. On the other hand, volatilization of the monomer components can be effectively restricted by heating the polymerizable composition to a temperature not higher than 150° C., for not longer than 120 min.

Examples of the photopolymerization initiator which is used in the case where the polymerizable composition is polymerized by the photopolymerization method include: phosphine oxide-based photopolymerization initiators such as 2,4,6-trimethylbenzoyl-diphenylphosphine oxide (TPO) and bis(2,4,6-trimethylbenzoyl)phenylphosphine oxide; benzoin-based photopolymerization initiators such as methyl orthobenzoylbenzoate, methyl benzoylformate, benzoin methyl ether, benzoin ethyl ether, benzoin isopropyl ether, benzoin isobutyl ether and benzoin n-butyl ether; phenone-based photopolymerization initiators such as 2-hydroxy-2-methyl-1-phenylpropane-1-one (HMPPO), p-isopropyl-α-hydroxyisobutylphenone, p-tert-butyltrichloroacetophenone, 2,2-dimethoxy-2-phenylacetophenone, α-α-dichloro-4-phenoxyacetophenone and N,N-tetraethyl-4,4-diaminobenzophenone; 1-hydroxycyclohexyl phenyl ketone; 1-phenyl-1,2-propanedione-2-(o-ethoxycarbonyl) oxime; thioxanthone-based photopolymerization initiators such as 2-chlorothioxanthone and 2-methylthioxanthone; dibenzosuberone; 2-ethylanthraquinone; benzophenone acrylate; benzophenone; and benzil. The above-indicated photopolymerization initiators may be used alone or in combination as a mixture of two or more of them. Further, the photosensitizer may be used together with the photopolymerization initiator. The photopolymerization initiator and the photosensitizer are used preferably in an amount of 0.001-2 parts by weight, and more preferably in an amount of 0.01-1 part by weight, per 100 parts by weight of the total amount of the monomer components in the polymerizable composition described above.

In the case of polymerizing the polymerizable composition by the photopolymerization method, it is necessary to select the photopolymerization initiator to be used depending on a range of the wavelength of the light with which the polymerizable composition is to be irradiated. An illumination intensity of the light is preferably set within a range of 0.1-100 $mW/cm^2$. The photopolymerization method may be conducted by stepwise irradiating the polymerizable composition with lights having respective different illumination intensities. The polymerizable composition is preferably irradiated with the light for a time period not shorter than 1 min. By setting the illumination intensity and the irradiation time as described above, it is possible to sufficiently cure the polymerizable composition, while preventing deterioration of the material of the casting mold (or the polymerization vessel). It is also possible to heat the polymerizable composition simultaneously with its irradiation with the light, whereby the polymerization reaction is promoted, and a copolymer can be easily formed. Although the material of the casting mold or the polymerization vessel is not particularly limited, as long as the light required for the polymerization (curing) of the polymerizable composition can be transmitted through the material, the material is preferably selected from general-purpose resins such as polypropylene, polystyrene, nylon and polyester, for example.

The thus obtained copolymer is usually subjected to a treatment for removing residues within the copolymer. For instance, in the bulk polymerization process, a viscosity of the system increases along with progress of the polymerization reaction, so that the monomer components cannot be dispersed within the system having a high viscosity, and the monomers which cannot be involved in the polymerization reaction and which are not polymerized often remain within the copolymer. On the other hand, in the solution polymerization process, a solvent which is not involved in the polymerization reaction often remains within the copolymer. Amounts of those residues within the contact lens, which is medical equipment, should be reduced as far as possible. Specifically, the residues are eluted from the copolymer by immersing the copolymer in water, an organic solvent or a mixture thereof, and preferably by repeating such an immersing operation. As the solvent used in the above-described treatment, it is also possible to use an aqueous solution such as an isotonic sodium chloride solution in which an inorganic compound is dissolved, and a mixed solution of such an aqueous solution and an organic solvent.

The copolymer subjected to the treatment for removing the residues is then subjected to a hydration treatment in which the copolymer is immersed in water, whereby the intended water-absorptive contact lens is obtained. It goes without saying that a sterilizing treatment or the like is appropriately performed on the thus obtained contact lens, so that a sufficiently high degree of safety of the contact lens with respect to a living body is secured.

Further, after formation of the contact lens by the above-described molding method, mechanical processing method or the like, various treatments for improving surface properties of the contact lens are performed on the contact lens in the dry state or the hydrated state, as necessary. Examples of the treatments for improving the surfaces properties of the contact lens include a low-temperature plasma treatment, an atmospheric-pressure plasma treatment, a corona discharge treatment or the like. For instance, by performing the low-temperature plasma treatment, it is possible to obtain the contact lens exhibiting more excellent wettability and/or anti-stain property. Specifically, the low-temperature plasma treatment can be performed in an atmosphere of a rarefied gas of alkane having 1 to 6 carbon atom(s), fluorine-substituted alkane having 1 to 6 carbon atom(s), nitrogen, oxygen, carbon dioxide, argon, hydrogen, air, water, silane or a mixture thereof. It is particularly preferable to perform the low-temperature plasma treatment in the rarefied gas atmosphere of oxygen alone, carbon dioxide alone, or a mixture of oxygen and water, tetrafluoromethane, an organic silane, methane, nitrogen or the like, since it is expected that the low-temperature plasma treatment performed in such an atmosphere gives a physical surface-modification effect by ion etching and a chemical surface-modification effect by ion implantation of radicals. The low-temperature plasma treatment can be performed under either of a reduced pressure and the atmospheric pressure. In the low-temperature plasma treatment, it is possible to control the surface-modification effects by appropriately adjusting output, a treatment time and a gas concentration, by using a high radio frequency (e.g. 13.65 MHz), a low audio frequency (e.g. 15.0-40.0 KHz) or a microwave (e.g. 2.45 GHz). In addition, it is also effective to perform a surface treatment using an ultraviolet ray, an eximer laser, an electron beam or the like, or to perform a surface-coating treatment using a hydrophilic agent such as 2-hydroxyethyl (meth)acrylate, (meth)acrylic acid, methoxytriethylene glycol (meth)acrylate, dimethyl acrylamide or the like, in order to make the surfaces of the contact lens hydrophilic and exhibit more excellent wettability.

EXAMPLES

To clarify the invention more specifically, some examples of the invention will be described. However, it goes without saying that the invention is by no means limited to the details of the illustrated examples. Further, it is to be understood that the invention may be embodied with various changes, modifications and improvements, which are not illustrated herein and which may occur to those skilled in the art, without departing from the spirit of the invention.

Abbreviations used in the illustrated examples indicate respective compounds described below.

TRIS: 3-[tris(trimethylsiloxy)silyl]propyl methacrylate
NVP: N-vinylpyrrolidone
DMAA: dimethyl acrylamide
N-MMP: 1-methyl-3-methylene-2-pyrrolidinone TPO: diphenyl(2,4,6-trimethylbenzoyl)phosphine oxide HMEPBT: 2-(2'-hydroxy-5'-(meth)acryloyloxyethylphenyl)-2H-benzotriazol HMPPO: 2-hydroxy-2-methyl-1-phenylpropane-1-one EDMA: ethyleneglycol dimethacrylate MTA: 2-methoxyethyl acrylate AMA: allyl methacrylate Initially, 16 kinds of polysiloxane-based macromonomer (macromonomers A through K and comparative macromonomers a through e) were synthesized by respective methods described below.

—Synthesis of Macromonomer A—

A 500 mL eggplant flask was charged with 107.48 g (95.96 mmol based on a functional group equivalent weight of 1120 g/mol) of a silicone which is modified with polypropylene oxide at both of its terminals, and available from Shin-Etsu Chemical Co., Ltd., JAPAN (Trade Name: X-22-4952; a number of repetition of an oxypropylene group is 10; a number of repetition of dimethylsiloxane is 20), and 26.64 g (119.85 mmol) of isophorone diisocyanate. The contents in the flask were stirred at the room temperature by using a stirrer, to dissolve the X-22-4952 in isophorone diisocyanate. Then, a solution obtained by dissolving 0.1427 g of tetrakis(2,4-pentanedionato)zirconium (IV) in 1.8248 g of acetonitrile was added to the contents in the flask, and the contents were stirred at the room temperature for 30 minutes. Further, 26.78 g (23.91 mmol based on the functional group equivalent weight of 1120 g/mol) of the X-22-4952 was added to the contents in the flask, a Dimroth condenser was attached to the flask, and the contents in the flask were stirred at 70° C. for 2 hours in an oil bath.

A solution obtained by dissolving 0.4265 g of p-methoxyphenol (MEHQ), 86.29 g (239.69 mmol) of polyethylene glycol monomethacrylate (average molecular weight: 360) and 0.1413 g of tetrakis(2,4-pentanedionato)zirconium (IV) in 1.8882 g of acetonitrile was added to the contents in the flask, and the contents were stirred at 70° C. for about 3 hours. A small amount of the thus obtained reaction solution was collected from the flask, and measured of an infrared absorption spectrum, whereby it was confirmed that a peak at 2350 cm$^{-1}$ corresponding to a NCO group was disappeared.

The reaction solution was dissolved in 800 mL of acetonitrile, and transferred into a separating funnel. Then, 800 mL of hexane was added to the reaction solution in the separating funnel to separate the reaction solution into layers. Among three layers of the thus separated reaction solution, the lowermost layer was discarded. Further, 200 mL of acetonitrile was added to the reaction solution to separate the reaction solution into layers again. Among three layers of the thus separated reaction solution, the lowermost layer was discarded. Further, 200 mL of acetonitrile was added to the reaction solution to separate the reaction solution into layers again. Among three layers of the thus separated reaction solution, the lowermost layer was discarded. Remaining layers of the reaction solution were collected, and 0.0117 g of 4-methoxy-1-naphthol (MNT) was added to the reaction solution. By distilling solvents away from the reaction solution under a reduced pressure, 103.55 g of a polysiloxane-based macromonomer (macromonomer A) in the form of a pale yellow liquid having a high viscosity was obtained. The macromonomer A has a structure represented by the above-indicated general formula (VIII), wherein $R^{51}$ is $CH_3$— (methyl group), a is 6, b is 10 and n is 19, and an HLB value of the macromonomer A calculated according to the above-indicated formula is 2.72.

—Synthesis of Macromonomer B—

A 500 mL eggplant flask was charged with 88.30 g (90.66 mmol based on a functional group equivalent weight of 974 g/mol) of a silicone which is modified with polypropylene oxide at both of its terminals (a number of repetition of an oxypropylene group is 5; a number of repetition of dimethylsiloxane is 20), and 50.37 g (226.61 mmol) of isophorone diisocyanate. The contents in the flask were stirred at the room temperature by using a stirrer, to dissolve the silicone in isophorone diisocyanate. Then, a solution obtained by dissolving 0.1750 g of tetrakis(2,4-pentanedionato)zirconium (IV) in 2.1474 g of acetonitrile was added to the contents in the flask, a Dimroth condenser was attached to the flask, and the contents in the flask were stirred at 70° C. for 1.5 hours in an oil bath.

A solution obtained by dissolving 0.8220 g of p-methoxyphenol (MEHQ), 163.28 g (453.56 mmol) of polyethylene glycol monomethacrylate (average molecular weight: 360) and 0.0886 g of tetrakis(2,4-pentanedionato)zirconium (IV) in 1.5612 g of acetonitrile was added to the contents in the flask, and the contents were stirred at 70° C. for 3 hours. A small amount of the thus obtained reaction solution was collected from the flask, and measured of an infrared absorption spectrum, whereby it was confirmed that a peak at 2350 cm$^{-1}$ corresponding to a NCO group was disappeared.

The reaction solution was dissolved in 600 mL of acetonitrile, and transferred into a separating funnel. Then, 600 mL of hexane was added to the reaction solution in the separating funnel to separate the reaction solution into layers. Among three layers of the thus separated reaction solution, the lowermost layer was discarded. Further, 300 mL of acetonitrile was added to the reaction solution to separate the reaction solution into layers again. Among three layers of the thus separated reaction solution, the lowermost layer was discarded. Further, 150 mL of acetonitrile was added to the reaction solution to separate the reaction solution into layers again. Among three layers of the thus separated reaction solution, the lowermost layer was discarded. Remaining layers of the reaction solution were collected, and 0.0093 g of 4-methoxy-1-naphthol (MNT) was added to the reaction solution. By distilling solvents away from the reaction solution under a reduced pressure, 67.67 g of a polysiloxane-based macromonomer (macromonomer B) in the form of a pale yellow liquid having a high viscosity was obtained. The macromonomer B has a structure represented by the above-indicated general formula (VIII), wherein $R^{51}$ is $CH_3$— (methyl group), a is 6, b is 5 and n is 19, and an HLB value of the macromonomer B calculated according to the above-indicated formula is 3.19.

—Synthesis of Macromonomer C—

A 500 mL eggplant flask was charged with 163.39 g (120.58 mmol based on a functional group equivalent weight of 1355 g/mol) of a silicone which is modified with polypropylene oxide at both of its terminals (a number of repetition of an oxypropylene group is 16; a number of repetition of dimethylsiloxane is 20), and 67.01 g (301.47 mmol) of isophorone diisocyanate. The contents in the flask were stirred at the room temperature by using a stirrer, to dissolve the silicone in isophorone diisocyanate. Then, a solution obtained by dissolving 0.3147 g of tetrakis(2,4-pentanedionato)zirconium (IV) in 3.1922 g of acetonitrile was added to the contents in the flask, a Dimroth condenser was attached to the flask, and the contents in the flask were stirred at 70° C. for 1.5 hours in an oil bath.

A solution obtained by dissolving 1.09 g of p-methoxyphenol (MEHQ), 218.70 g (607.5 mmol) of polyethylene glycol monomethacrylate (average molecular weight: 360)

and 0.1043 g of tetrakis(2,4-pentanedionato)zirconium (IV) in 1.5178 g of acetonitrile was added to the contents in the flask, and the contents were stirred at 70° C. for 2 hours. A small amount of the thus obtained reaction solution was collected from the flask, and measured of an infrared absorption spectrum, whereby it was confirmed that a peak at 2350 $cm^{-1}$ corresponding to a NCO group was disappeared.

The reaction solution was dissolved in 800 mL of acetonitrile, and transferred into a separating funnel. Then, 800 mL of hexane was added to the reaction solution in the separating funnel to separate the reaction solution into layers. Among three layers of the thus separated reaction solution, the lowermost layer was discarded. Further, 400 mL of acetonitrile was added to the reaction solution to separate the reaction solution into layers again. Among three layers of the thus separated reaction solution, the lowermost layer was discarded. Further, 200 mL of acetonitrile was added to the reaction solution to separate the reaction solution into layers again. Among three layers of the thus separated reaction solution, the lowermost layer was discarded. Remaining layers of the reaction solution were collected, and 0.0122 g of 4-methoxy-1-naphthol (MNT) was added to the reaction solution. By distilling solvents away from the reaction solution under a reduced pressure, 67.67 g of a pale yellow liquid having a high viscosity was obtained.

An SEC (size exclusion chromatography) analysis was conducted on the thus obtained pale yellow liquid, whereby a peak which is considered to correspond to a reaction reagent or a byproduct was observed after a peak of a macromonomer. Therefore, the liquid was separated into layers again by using 600 mL of hexane and 600 mL of acetonitrile. As a result, the lowermost layer of the thus separated liquid was constituted by a layer (which is pale yellow and which has a high viscosity) which had been located in the middle of the three layers in the previously performed separating operations. The uppermost layer was constituted by hexane. Accordingly, the intermediate layer was constituted by acetonitrile.

After discarding the layer of acetonitrile, 400 mL of acetonitrile was added to the above-described liquid to separate the liquid into layers again. By collecting the lowermost layer of the thus separated liquid, and distilling solvents away from the liquid under a reduced pressure, 76.76 g of a polysiloxane-based macromonomer (macromonomer C) in the form of a pale yellow liquid having a high viscosity was obtained. The macromonomer C has a structure represented by the above-indicated general formula (VIII), wherein $R^{51}$ is $CH_3$— (methyl group), a is 6, b is 16 and n is 19, and an HLB value of the macromonomer C calculated according to the above-indicated formula is 2.30.

—Synthesis of Macromonomer D—

A 500 mL eggplant flask was charged with 152.56 g (80.08 mmol based on a functional group equivalent weight of 1905 g/mol) of a silicone which is modified with polypropylene oxide at both of its terminals (a number of repetition of an oxypropylene group is 16; a number of repetition of dimethylsiloxane is 40), and 44.53 g (200.33 mmol) of isophorone diisocyanate. The contents in the flask were stirred at the room temperature by using a stirrer, to dissolve the silicone in isophorone diisocyanate. Then, a solution obtained by dissolving 0.2989 g of tetrakis(2,4-pentanedionato)zirconium (IV) in 3.1234 g of acetonitrile was added to the contents in the flask, a Dimroth condenser was attached to the flask, and the contents in the flask were stirred at 70° C. for 1.5 hours in an oil bath.

A solution obtained by dissolving 0.72 g of p-methoxyphenol (MEHQ), 144.26 g (400.72 mmol) of polyethylene glycol monomethacrylate (average molecular weight: 360) and 0.1059 g of tetrakis(2,4-pentanedionato)zirconium (IV) in 1.7584 g of acetonitrile was added to the contents in the flask, and the contents were stirred at 70° C. for 1.5 hours. A small amount of the thus obtained reaction solution was collected from the flask, and measured of an infrared absorption spectrum, whereby it was confirmed that a peak at 2350 $cm^{-1}$ corresponding to a NCO group was disappeared.

The reaction solution was dissolved in 1000 mL of acetonitrile, and transferred into a separating funnel. Then, 1000 mL of hexane was added to the reaction solution in the separating funnel to separate the reaction solution into layers. Among two layers of the thus separated reaction solution, a lower layer (layer of acetonitrile) was discarded. Further, 400 mL of acetonitrile was added to the reaction solution to separate the reaction solution into layers again. Among two layers of the thus separated reaction solution, a lower layer was discarded. Further, 400 mL of acetonitrile was added to the reaction solution to separate the reaction solution into layers again. Among two layers of the thus separated reaction solution, a lower layer was discarded. A remaining layer of the reaction solution was collected, and 0.0120 g of 4-methoxy-1-naphthol (MNT) was added to the reaction solution. By distilling solvents away from the reaction solution under a reduced pressure, 100.24 g of a polysiloxane-based macromonomer (macromonomer D) in the form of a liquid having a high viscosity was obtained. The macromonomer D has a structure represented by the above-indicated general formula (VIII), wherein $R^{51}$ is $CH_3$— (methyl group), a is 6, b is 16 and n is 39, and an HLB value of the macromonomer D calculated according to the above-indicated formula is 1.74.

—Synthesis of Macromonomer E—

A 500 mL eggplant flask was charged with 112.30 g (73.78 mmol based on a functional group equivalent weight of 1522 g/mol) of a silicone which is modified with polypropylene oxide at both of its terminals (a number of repetition of an oxypropylene group is 5; a number of repetition of dimethylsiloxane is 40), and 41.01 g (184.50 mmol) of isophorone diisocyanate. The contents in the flask were stirred at the room temperature by using a stirrer, to dissolve the silicone in isophorone diisocyanate. Then, a solution obtained by dissolving 0.2009 g of tetrakis(2,4-pentanedionato)zirconium (IV) in 1.9901 g of acetonitrile was added to the contents in the flask, a Dimroth condenser was attached to the flask, and the contents in the flask were stirred at 70° C. for 1.5 hours in an oil bath.

A solution obtained by dissolving 0.67 g of p-methoxyphenol (MEHQ), 132.76 g (368.78 mmol) of polyethylene glycol monomethacrylate (average molecular weight: 360) and 0.1013 g of tetrakis(2,4-pentanedionato)zirconium (IV) in 1.4989 g of acetonitrile was added to the contents in the flask, and the contents were stirred at 70° C. for 3 hours. A small amount of the thus obtained reaction solution was collected from the flask, and measured of an infrared absorption spectrum, whereby it was confirmed that a peak at 2350 $cm^{-1}$ corresponding to a NCO group was disappeared.

The reaction solution was dissolved in 800 mL of acetonitrile, and transferred into a separating funnel. Then, 800 mL of hexane was added to the reaction solution in the separating funnel to separate the reaction solution into layers. Among two layers of the thus separated reaction solution, a lower layer (layer of acetonitrile) was discarded. Further, 400 mL of acetonitrile was added to the reaction solution to separate the reaction solution into layers again. Among two layers of the thus separated reaction solution, a lower layer was discarded. Further, 400 mL of acetonitrile was added to the reaction solution to separate the reaction solution into layers again. Among two layers of the thus separated reaction solution, a lower layer was discarded. A remaining layer of the reaction solution was collected, and 0.0120 g of 4-methoxy-1-naphthol (MNT) was added to the reaction solution. By distilling solvents away from the reaction solution under a reduced pressure, 110.44 g of a polysiloxane-based macromonomer (macromonomer E) in the form of a liquid having a high viscosity was obtained. The macromonomer E has a structure represented by the above-indicated general formula (VIII), wherein $R^{51}$ is $CH_3$— (methyl group), a is 6, b is 5 and n is 39, and an HLB value of the macromonomer E calculated according to the above-indicated formula is 2.21.

—Synthesis of Macromonomer F—

A 500 mL eggplant flask was charged with 115.53 g (67.52 mmol based on a functional group equivalent weight of 1711 g/mol) of a silicone which is modified with polypropylene oxide at both of its terminals (a number of repetition of an oxypropylene group is 10; a number of repetition of dimethylsiloxane is 40), and 37.52 g (168.80 mmol) of isophorone diisocyanate. The contents in the flask were stirred at the room temperature by using a stirrer, to dissolve the silicone in isophorone diisocyanate. Then, a solution obtained by dissolving 0.2035 g of tetrakis(2,4-pentanedionato)zirconium (IV) in 2.5868 g of acetonitrile was added to the contents in the flask, a Dimroth condenser was attached to the flask, and the contents in the flask were stirred at 70° C. for 1.5 hours in an oil bath.

A solution obtained by dissolving 0.61 g of p-methoxyphenol (MEHQ), 121.27 g (336.86 mmol) of polyethylene glycol monomethacrylate (average molecular weight: 360) and 0.1089 g of tetrakis(2,4-pentanedionato)zirconium (IV) in 1.7292 g of acetonitrile was added to the contents in the flask, and the contents were stirred at 70° C. for about 1 hour. A small amount of the thus obtained reaction solution was collected from the flask, and measured of an infrared absorption spectrum, whereby it was confirmed that a peak at 2350 $cm^{-1}$ corresponding to a NCO group was disappeared.

The reaction solution was dissolved in 800 mL of acetonitrile, and transferred into a separating funnel. Then, 800 mL of hexane was added to the reaction solution in the separating funnel to separate the reaction solution into layers. Among two layers of the thus separated reaction solution, a lower layer (layer of acetonitrile) was discarded. Further, 400 mL of acetonitrile was added to the reaction solution to separate the reaction solution into layers again. Among two layers of the thus separated reaction solution, a lower layer was discarded. Further, 400 mL of acetonitrile was added to the reaction solution to separate the reaction solution into layers again. Among two layers of the thus separated reaction solution, a lower layer was discarded. A remaining layer of the reaction solution was collected, and 0.0114 g of 4-methoxy-1-naphthol (MNT) was added to the reaction solution. By distilling solvents away from the reaction solution under a reduced pressure, 105.13 g of a polysiloxane-based macromonomer (macromonomer F) in the form of a liquid having a high viscosity was obtained. The macromonomer F has a structure represented by the above-indicated general formula (VIII), wherein $R^{51}$ is $CH_3$— (methyl group), a is 6, b is 10 and n is 39, and an HLB value of the macromonomer F calculated according to the above-indicated formula is 1.97.

—Synthesis of Macromonomer G—

A 500 mL eggplant flask was charged with 121.95 g (54.03 mmol based on a functional group equivalent weight of 2257 g/mol) of a silicone which is modified with polypropylene oxide at both of its terminals (a number of repetition of an oxypropylene group is 10; a number of repetition of dimethylsiloxane is 60), and 30.10 g (135.41 mmol) of isophorone diisocyanate. The contents in the flask were stirred at the room temperature by using a stirrer, to dissolve the silicone in isophorone diisocyanate. Then, a solution obtained by dissolving 0.2130 g of tetrakis(2,4-pentanedionato)zirconium (IV) in 2.6731 g of acetonitrile was added to the contents in the flask, a Dimroth condenser was attached to the flask, and the contents in the flask were stirred at 70° C. for 1.5 hours in an oil bath.

A solution obtained by dissolving 0.48 g of p-methoxyphenol (MEHQ), 99.90 g (277.50 mmol) of polyethylene glycol monomethacrylate (average molecular weight: 360) and 0.1092 g of tetrakis(2,4-pentanedionato)zirconium (IV) in 2.0494 g of acetonitrile was added to the contents in the flask, and the contents were stirred at 70° C. for 1 hour. A small amount of the thus obtained reaction solution was collected from the flask, and measured of an infrared absorption spectrum, whereby it was confirmed that a peak at 2350 $cm^{-1}$ corresponding to a NCO group was disappeared.

The reaction solution was dissolved in 800 mL of acetonitrile, and transferred into a separating funnel. Then, 800 mL of hexane was added to the reaction solution in the separating funnel to separate the reaction solution into layers. Among two layers of the thus separated reaction solution, a lower layer (layer of acetonitrile) was discarded. Further, 400 mL of acetonitrile was added to the reaction solution to separate the reaction solution into layers again. Among two layers of the thus separated reaction solution, a lower layer was discarded. Further, 400 mL of acetonitrile was added to the reaction solution to separate the reaction solution into layers again. Among two layers of the thus separated reaction solution, a lower layer was discarded. A remaining layer of the reaction solution was collected, and 0.0119 g of 4-methoxy-1-naphthol (MNT) was added to the reaction solution. By distilling solvents away from the reaction solution under a reduced pressure, 121.29 g of a polysiloxane-based macromonomer (macromonomer G) in the form of a liquid having a high viscosity was obtained. The macromonomer G has a structure represented by the above-indicated general formula (VIII), wherein $R^{51}$ is $CH_3$— (methyl group), a is 6, b is 10 and n is 59, and an HLB value of the macromonomer G calculated according to the above-indicated formula is 1.54.

—Synthesis of Macromonomer H—

A 500 mL eggplant flask was charged with 115.11 g (67.27 mmol based on a functional group equivalent weight of 1711 g/mol) of a silicone which is modified with polypropylene oxide at both of its terminals (a number of repetition of an oxypropylene group is 10; a number of repetition of dimethylsiloxane is 40), and 37.38 g (168.17 mmol) of isophorone diisocyanate. The contents in the flask were stirred at the room temperature by using a stirrer, to dissolve the silicone in isophorone diisocyanate. Then, a solution obtained by dissolving 0.2001 g of tetrakis(2,4-pentanedionato)zirconium (IV) in 2.5765 g of acetonitrile was added to the contents in the flask, a Dimroth condenser was attached to the flask, and the contents in the flask were stirred at 70° C. for 1.5 hours in an oil bath.

A solution obtained by dissolving 0.61 g of p-methoxyphenol (MEHQ), 152.69 g (336.32 mmol) of polyethylene glycol monomethacrylate (average molecular weight: 526)

and 0.1079 g of tetrakis(2,4-pentanedionato)zirconium (IV) in 1.8233 g of acetonitrile was added to the contents in the flask, and the contents were stirred at 70° C. for about 1 hour. A small amount of the thus obtained reaction solution was collected from the flask, and measured of an infrared absorption spectrum, whereby it was confirmed that a peak at 2350 cm$^{-1}$ corresponding to a NCO group was disappeared.

The reaction solution was dissolved in 800 mL of acetonitrile, and transferred into a separating funnel. Then, 800 mL of hexane was added to the reaction solution in the separating funnel to separate the reaction solution into layers. Among two layers of the thus separated reaction solution, a lower layer (layer of acetonitrile) was discarded. Further, 400 mL of acetonitrile was added to the reaction solution to separate the reaction solution into layers again. Among two layers of the thus separated reaction solution, a lower layer was discarded. Further, 400 mL of acetonitrile was added to the reaction solution to separate the reaction solution into layers again. Among two layers of the thus separated reaction solution, a lower layer was discarded. A remaining layer of the reaction solution was collected, and 0.0112 g of 4-methoxy-1-naphthol (MNT) was added to the reaction solution. By distilling solvents away from the reaction solution under a reduced pressure, 100.13 g of a polysiloxane-based macromonomer (macromonomer H) in the form of a liquid having a high viscosity was obtained. The macromonomer H has a structure represented by the above-indicated general formula (VIII), wherein R$^{51}$ is CH$_3$— (methyl group), a is 10, b is 10 and n is 39, and an HLB value of the macromonomer H calculated according to the above-indicated formula is 3.08.

—Synthesis of Macromonomer I—

A 500 mL eggplant flask was charged with 98.20 g (100.82 mmol based on a functional group equivalent weight of 974 g/mol) of a silicone which is modified with polypropylene oxide at both of its terminals (a number of repetition of an oxypropylene group is 5; a number of repetition of dimethylsiloxane is 20), and 56.03 g (252.07 mmol) of isophorone diisocyanate. The contents in the flask were stirred at the room temperature by using a stirrer, to dissolve the silicone in isophorone diisocyanate. Then, a solution obtained by dissolving 0.1730 g of tetrakis(2,4-pentanedionato)zirconium (IV) in 2.2347 g of acetonitrile was added to the contents in the flask, a Dimroth condenser was attached to the flask, and the contents in the flask were stirred at 70° C. for 1.5 hours in an oil bath.

A solution obtained by dissolving 1.32 g of p-methoxyphenol (MEHQ), 265.18 g (504.14 mmol) of polyethylene glycol monomethacrylate (average molecular weight: 526) and 0.0986 g of tetrakis(2,4-pentanedionato)zirconium (IV) in 1.8672 g of acetonitrile was added to the contents in the flask, and the contents were stirred at 70° C. for about 1 hour. A small amount of the thus obtained reaction solution was collected from the flask, and measured of an infrared absorption spectrum, whereby it was confirmed that a peak at 2350 cm$^{-1}$ corresponding to a NCO group was disappeared.

The reaction solution was dissolved in 800 mL of acetonitrile, and transferred into a separating funnel. Then, 800 mL of hexane was added to the reaction solution in the separating funnel to separate the reaction solution into layers. Among two layers of the thus separated reaction solution, a lower layer (layer of acetonitrile) was discarded. Further, 400 mL of acetonitrile was added to the reaction solution to separate the reaction solution into layers again. Among two layers of the thus separated reaction solution, a lower layer was discarded. Further, 400 mL of acetonitrile was added to the reaction solution to separate the reaction solution into layers again. Among two layers of the thus separated reaction solution, a lower layer was discarded. A remaining layer of the reaction solution was collected, and 0.0134 g of 4-methoxy-1-naphthol (MNT) was added to the reaction solution. By distilling solvents away from the reaction solution under a reduced pressure, 74.48 g of a polysiloxane-based macromonomer (macromonomer I) in the form of a liquid having a high viscosity was obtained. The macromonomer I has a structure represented by the above-indicated general formula (VIII), wherein R$^{51}$ is CH$_3$— (methyl group), a is 10, b is 5 and n is 19, and an HLB value of the macromonomer I calculated according to the above-indicated formula is 4.81.

—Synthesis of Macromonomer J—

A 1 L flask was charged with 294.6 g (0.1 mol) of dimethylpolysiloxane containing SiH groups at both of its terminals (a number of Si atoms is 40), 216.5 g (0.24 mol) of a copolymer of hexaethylene oxide and decapropylene oxide which is modified with an allyl group at its terminal, and 200 g of isopropyl alcohol, and a reaction was conducted for 4 hours under reflux of isopropyl alcohol, by using 0.03 g of a 3% ethanol solution of a neutralized chloroplatinic complex with vinyl siloxane, as a catalyst. After the reaction, it was confirmed that the SiH groups in dimethylpolysiloxane were completely disappeared.

By removing isopropyl alcohol under a reduced pressure, 500 g of a reaction product was obtained. Then, in order to remove the copolymer of hexaethylene oxide and decapropylene oxide which is modified with the allyl group at its terminal, remaining in the reaction product, the reaction product was reprecipitated by using 600 g of acetonitrile. Thereafter, a lower layer constituted by siloxane was collected, and further reprecipitated twice by using acetonitrile, whereby 420 g of a silicone which has polyether at both of its terminals and which does not contain unreacted polyether was obtained.

A 500 mL flask was charged with 237.5 g (0.05 mol) of the thus obtained silicone having polyether at both of its terminals, 0.03 g of iron acetylacetone, 0.15 g of dibutyl hydroxytoluene (BHT) and 0.6 g of p-methoxyphenol, and the contents in the flask were stirred at the room temperature for 1 hour, to disperse iron acetylacetone in the silicone. Then, 28.2 g (0.2 mol) of acryloylethyl isocyanate (Trade Name: Karenz AOI; available from SHOWA DENKO K.K., JAPAN) was dropped into the flask by using a dropping funnel. The flask was left at 40° C. for 3 hours, to complete an urethanization reaction.

Thereafter, acryloylethyl isocyanate remaining in the reaction solution was deactivated by using methanol. The thus obtained silicone solution was dissolved in an amount of hexane equal to that of the silicone solution, and the thus obtained hexane solution was washed three times by using acetonitrile which was used in the same amount as hexane. Then, 0.03 g of dibutyl hydroxytoluene (BHT) was added to an upper layer (layer of hexane) of the reaction solution which had been washed as described above. By distilling hexane away from the reaction solution under a reduced pressure, 203 g of a polysiloxane-based macromonomer (macromonomer J) in the form of a colorless and transparent liquid was obtained. The macromonomer J has a structure represented by the above-indicated general formula (IX), wherein a' is 6, b' is 10 and n is 39, and an HLB value of the macromonomer J calculated according to the above-indicated formula is 2.10.

—Synthesis of Macromonomer K—

A 500 mL eggplant flask was charged with 122.97 g (71.87 mmol based on a functional group equivalent weight of 1711 g/mol) of a silicone which is modified with polypropylene oxide at both of its terminals (a number of repetition of an oxypropylene group is 10; a number of repetition of dimethylsiloxane is 40), and 39.94 g (179.68 mmol) of isophorone diisocyanate. The contents in the flask were stirred at the room temperature by using a stirrer, to dissolve the silicone in isophorone diisocyanate. Then, a solution obtained by dissolving 0.2113 g of tetrakis(2,4-pentanedionato)zirconium (IV) in 3.1027 g of acetonitrile was added to the contents in the flask, a Dimroth condenser was attached to the flask, and the contents in the flask were stirred at 70° C. for 1.5 hours in an oil bath.

A solution obtained by dissolving 0.65 g of p-methoxyphenol (MEHQ), 153.17 g (510.57 mmol) of polyethylene glycol monomethacrylate (average molecular weight: 300) and 0.1089 g of tetrakis(2,4-pentanedionato)zirconium (IV) in 1.7292 g of acetonitrile was added to the contents in the flask, and the contents were stirred at 70° C. for about 1 hour. A small amount of the thus obtained reaction solution was collected from the flask, and measured of an infrared absorption spectrum, whereby it was confirmed that a peak at 2350 $cm^{-1}$ corresponding to a NCO group was disappeared.

The reaction solution was dissolved in 800 mL of acetonitrile, and transferred into a separating funnel. Then, 800 mL of hexane was added to the reaction solution in the separating funnel to separate the reaction solution into layers. Among two layers of the thus separated reaction solution, a lower layer (layer of acetonitrile) was discarded. Further, 400 mL of acetonitrile was added to the reaction solution to separate the reaction solution into layers again. Among two layers of the thus separated reaction solution, a lower layer was discarded. Further, 400 mL of acetonitrile was added to the reaction solution to separate the reaction solution into layers again. Among two layers of the thus separated reaction solution, a lower layer was discarded. A remaining layer of the reaction solution was collected, and 0.0122 g of 4-methoxy-1-naphthol (MNT) was added to the reaction solution. By distilling solvents away from the reaction solution under a reduced pressure, 98.04 g of a polysiloxane-based macromonomer (macromonomer K) in the form of a liquid having a high viscosity was obtained. The macromonomer K has a structure represented by the above-indicated general formula (VIII), wherein $R^{51}$ is $CH_3$— (methyl group), a is 4, b is 10 and n is 39, and an HLB value of the macromonomer K calculated according to the above-indicated formula is 1.51.

—Synthesis of Comparative Macromonomer a—

A 500 mL eggplant flask was charged with 95.25 g (91.85 mmol based on a functional group equivalent weight of 1037 g/mol) of a silicone which is modified with polyethylene oxide at both of its terminals, and available from Shin-Etsu Chemical Co., Ltd. (Trade Name: X-22-4272; a number of repetition of an oxyethylene group is 10; a number of repetition of dimethylsiloxane is 20), and 25.60 g (115.2 mmol) of isophorone diisocyanate. The contents in the flask were stirred at the room temperature by using a stirrer, to dissolve the X-22-4272 in isophorone diisocyanate. Then, a solution obtained by dissolving 0.1439 g of tetrakis(2,4-pentanedionato)zirconium (IV) in 1.54 g of acetonitrile was added to the contents in the flask, and the contents were stirred at the room temperature for 30 minutes. Further, 24.20 g (23.33 mmol based on the functional group equivalent weight of 1037 g/mol) of the X-22-4272 was added to the contents in the flask, a Dimroth condenser was attached to the flask, and the contents in the flask were stirred at 70° C. for 1 hour in an oil bath.

A solution obtained by dissolving 83.50 g (231.94 mmol) of polyethylene glycol monomethacrylate (average molecular weight: 360) and 0.1503 g of tetrakis(2,4-pentanedionato)zirconium (IV) in 1.63 g of acetonitrile was added to the contents in the flask, and the contents were stirred at 70° C. for 3 hours. A small amount of the thus obtained reaction solution was collected from the flask, and measured of an infrared absorption spectrum, whereby it was confirmed that a peak at 2350 $cm^{-1}$ corresponding to a NCO group was disappeared.

The reaction solution was dissolved in 1000 mL of acetonitrile, and transferred into a separating funnel. Then, 1000 mL of hexane was added to the reaction solution in the separating funnel to separate the reaction solution into layers. Among three layers of the thus separated reaction solution, the lowermost layer was discarded. Further, 400 mL of acetonitrile was added to the reaction solution to separate the reaction solution into layers again. Among three layers of the thus separated reaction solution, the lowermost layer was discarded. Further, 600 mL of acetonitrile was added to the reaction solution to separate the reaction solution into layers again. Among three layers of the thus separated reaction solution, the lowermost layer was discarded. The lowermost layer of remaining layers of the reaction solution was collected, and 0.0221 g of 4-methoxy-1-naphthol (MNT) was added to the reaction solution. By distilling solvents away from the reaction solution under a reduced pressure, 51.67 g of a polysiloxane-based macromonomer (comparative macromonomer a) in the form of an yellow liquid having a high viscosity was obtained. The comparative macromonomer a has a structure represented by the above-indicated general formula (VIII), wherein $R^{51}$ is $CH_3$— (methyl group), a is 6, the part indicated as ( ... )$_b$ is a polyoxyethylene chain having an oxyethylene group as a repeating unit (a number of repetition is 10), and n is 19, and an HLB value of the comparative macromonomer a calculated according to the above-indicated formula is 7.81.

—Synthesis of Comparative Macromonomer b—

A 500 mL eggplant flask was charged with 110.79 g (98.91 mmol based on a functional group equivalent weight of 1120 g/mol) of a silicone which is modified with polypropylene oxide at both of its terminals, and available from Shin-Etsu Chemical Co., Ltd. (Trade Name; X-22-4952; a number of repetition of an oxypropylene group is 10; a number of repetition of dimethylsiloxane is 20), and 33.08 g (148.8 mmol) of isophorone diisocyanate. The contents in the flask were stirred at the room temperature by using a stirrer, to dissolve the X-22-4952 in isophorone diisocyanate. Then, a solution obtained by dissolving 0.1799 g of tetrakis(2,4-pentanedionato)zirconium (IV) in 1.74 g of acetonitrile was added to the contents in the flask, and the contents were stirred at the room temperature for 30 minutes. Further, 33.55 g (29.96 mmol based on the functional group equivalent weight of 1120 g/mol) of the X-22-4952 was added to the contents in the flask, and the contents in the flask were stirred at the room temperature for 25 minutes. Thereafter, a Dimroth condenser was attached to the flask, and the contents in the flask were stirred at 70° C. for 2 hours in an oil bath. Then, a small amount of the thus obtained reaction solution was collected from the flask, and measured of $^1$HNMR, whereby it was confirmed that a signal (at about 3.1 ppm) of $CH_2$ adjacent to a primary NCO group of isophorone diisocyanate was almost disappeared.

After adding 0.5641 g of p-methoxyphenol (MEHQ) and 42.86 g (297.3 mmol) of 4-hydroxybutyl acrylate to the reaction solution in the flask, the reaction solution was stirred at 70° C. for 1 hour. A small amount of the thus obtained reaction solution was collected from the flask, and measured of an infrared absorption spectrum, whereby it was confirmed that a peak at 2350 cm$^{-1}$ corresponding to a NCO group was disappeared.

The reaction solution was dissolved in 800 mL of acetonitrile, and transferred into a separating funnel. Then, 800 mL of hexane was added to the reaction solution in the separating funnel to separate the reaction solution into layers. Among two layers of the thus separated reaction solution, a lower layer was discarded. Further, 400 mL of acetonitrile was added to the reaction solution to separate the reaction solution into layers again. Among two layers of the thus separated reaction solution, a lower layer was discarded. Further, 400 mL of acetonitrile was added to the reaction solution to separate the reaction solution into layers again. Among two layers of the thus separated reaction solution, a lower layer was discarded. A remaining layer of the reaction solution was collected, and 0.0110 g of 4-methoxy-1-naphthol (MNT) was added to the reaction solution. By distilling solvents away from the reaction solution under a reduced pressure, 127.5 g of a polysiloxane-based macromonomer (comparative macromonomer b) in the form of a liquid having a high viscosity was obtained. The comparative macromonomer b has a structure represented by the above-indicated general formula (VIII), wherein R is H— (hydrogen atom), the part indicated as ( . . . )$_a$ is a butylene group (—$CH_2CH_2CH_2CH_2$—), b is 10 and n is 19, and an HLB value of the comparative macromonomer b calculated according to the above-indicated formula is 0.65.

—Synthesis of Comparative Macromonomer c—

A polysiloxane-based macromonomer (comparative macromonomer c) represented by a structural formula (X) given below was synthesized by a method similar to that used in Example 1 described in JP-A-2001-72739. An HLB value of the comparative macromonomer c calculated according to the above-indicated formula is 0.46.

—Synthesis of Comparative Macromonomer d—

A 1 L flask was charged with 146.6 g (0.1 mol) of dimethylpolysiloxane containing SiH groups at both of its terminals (a number of Si atoms is 20), 153.1 g (0.24 mol) of decapropylene oxide which is modified with an allyl group at its terminal (a number of repetition of an oxypropylene group is 10), and 150 g of isopropyl alcohol, and a reaction was conducted for 4 hours under reflux of isopropyl alcohol, by using 0.03 g of a 3% ethanol solution of a neutralized chloroplatinic complex with vinyl siloxane, as a catalyst. After the reaction, it was confirmed that the SiH groups in dimethylpolysiloxane were completely disappeared.

By removing isopropyl alcohol under a reduced pressure, 280 g of a reaction product was obtained. Then, in order to remove decapropylene oxide which is modified with the allyl group at its terminal, remaining in the reaction product, the reaction product was reprecipitated by using 500 g of acetonitrile. Thereafter, a lower layer constituted by siloxane was collected, and further reprecipitated twice by using acetonitrile, whereby 220 g of a silicone which has polyether at both of its terminals and which does not contain unreacted polyether was obtained.

A 500 mL flask was charged with 137.1 g (0.05 mol) of the thus obtained silicone having polyether at both of its terminals, 0.02 g of iron acetylacetone, 0.1 g of dibutyl hydroxytoluene (BHT) and 0.4 g of p-methoxyphenol, and the contents in the flask were stirred at the room temperature for 1 hour, to disperse iron acetylacetone in the silicone. Then, 28.2 g (0.2 mol) of acryloylethyl isocyanate (Trade Name: Karenz AOI; available from SHOWA DENKO K.K.) was dropped into the flask by using a dropping funnel. The flask was left at 40° C. for 3 hours, to complete an urethanization reaction.

Thereafter, acryloylethyl isocyanate remaining in the reaction solution was deactivated by using methanol. The thus obtained silicone solution was reprecipitated three times, by using 450 g of methanol and 90 g of water for each time of the reprecipitation. By removing the lowermost layer of the silicone solution reprecipitated as described above, 100 g of a polysiloxane-based macromonomer (comparative macromonomer d) in the form of a colorless and transparent liquid was obtained. The comparative macromonomer d is represented by a structural formula (XI) given below, and has an HLB value of the comparative macromonomer d calculated according to the above-indicated formula is 0.57.

[Chemical Formula 5]

Structural Formula (X)

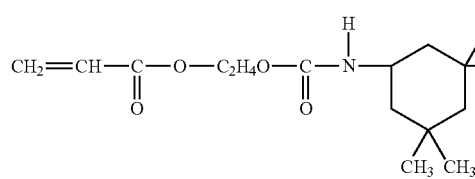
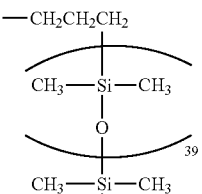
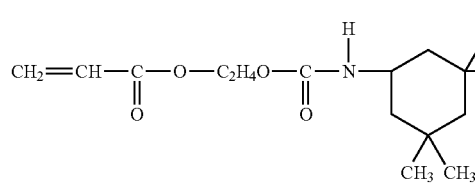
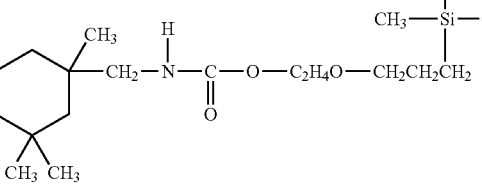

[Chemical Formula 6]

Structural Formula (XI)

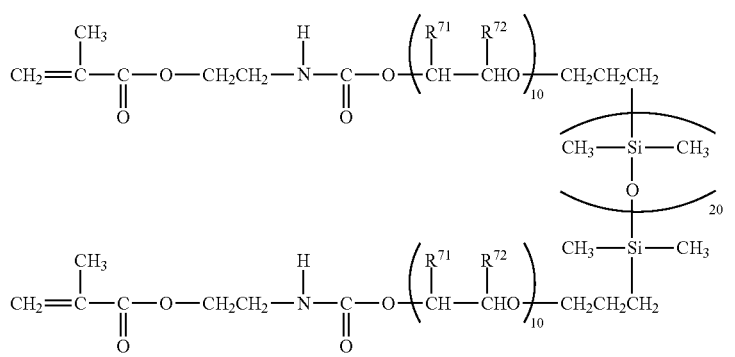

(In the above-indicated structural formula (XI), each of $R^{71}$ and $R^{72}$ is a hydrogen atom or a methyl group, wherein $R^{72}$ is the methyl group in the case where $R^{71}$ is the hydrogen atom, and $R^{72}$ is the hydrogen atom in the case where $R^{71}$ is the methyl group.)

—Synthesis of Comparative Macromonomer e—

A 3 L flask was charged with 193 g (0.5 mol) of 1,1,3,3-tetramethyl-1,3-methacryloxypropyl-disiloxane, 1480 g (5 mol) of octamethyl cyclotetrasiloxane and 0.28 g of trifluoromethanesulfonic acid, and the contents in the flask were reacted with each other at the room temperature for 5 hours. Then, 56 g of sodium bicarbonate was added to the thus obtained reaction solution in the flask, and the reaction solution was neutralized at the room temperature for 2 hours. Thereafter, the reaction solution was purified by filtration.

By adding 0.06 g of dibutyl hydroxytoluene (BHT) to the thus filtered reaction solution, and removing dimethyl cyclics generated as a by-product at a temperature of 120° C., 1500 g of a comparative macromonomer e was obtained. The comparative macromonomer e is represented by a structural formula (XII) given below, and an HLB value of the comparative macromonomer e calculated according to the above-indicated formula is 0.52.

[Chemical Formula 7]

Structural Formula (XII)

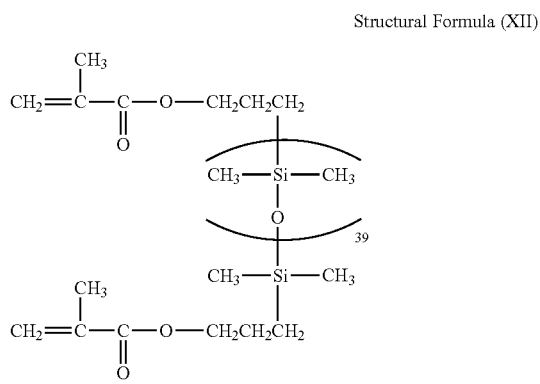

The polysiloxane-based macromonomers synthesized as described above were tested as described below.

—Compatibility Test I—

Each one of the macromonomers A through H and the comparative macromonomer a was mixed with each one of TRIS, which is a silicone monomer, and NVP, which is a hydrophilic monomer, at a ratio of 1:1 (weight ratio), and a state of mixing of each macromonomer with TRIS and NVP was visually observed. As a result, it was found that a transparent solution was obtained by mixing any one of the macromonomers A through H according to the invention, with either of TRIS and NVP. On the other hand, it was recognized that a transparent solution was obtained by mixing the comparative macromonomer a with NVP, but a solution obtained by mixing the comparative macromonomer a with TRIS was clouded, presumably due to excessively high hydrophilicity of the comparative macromonomer a.

—Compatibility Test II—

Polymerizable compositions (polymerization liquids) were prepared by using each one of the macromonomer F and the comparative macromonomer c, as the polysiloxane-based macromonomer, and other components which were mixed with the macromonomer F and the comparative macromonomer c in respective proportions indicated in Table 1 given below. A state of mixing of the components of the polymerization liquids was visually observed. Results of the observation are indicated in Table 1.

TABLE 1

| Proportion (part by weight) | Macromonomer F | 10 | — |
|---|---|---|---|
| | Comparative Macromonomer c | — | 10 |
| | NVP | 50 | 50 |
| | MTA | 40 | 40 |
| | AMA | 0.5 | 0.5 |
| | TPO | 1 | 1 |
| Appearance of Polymerization Liquid | | Transparent | Clouded |

As is apparent from the results indicated in Table 1, the polymerization liquid did not clouded in the case where the macromonomer F according to the invention was used, whereas the polymerization liquid was clouded in the case where the comparative macromonomer c was used.

—Compatibility Test III—

A polymerizable composition (polymerization liquid) was prepared by mixing 35 parts by weight of the macromonomer K according to the invention, 25 parts by weight of TRIS, 25 parts by weight of N-MMP, 25 parts by weight of DMAA, 2 parts by weight of HMEPBT, and 0.3 part by weight of TPO. A state of mixing of the components of the polymerization liquid was visually observed, whereby it was found that the polymerization liquid was transparent and not clouded.

—Compatibility Test IV—

Initially, there were prepared polymerizable compositions (polymerization liquids; Examples 1 to 23 and Comparative Examples 1 to 6) including components at respective proportions indicated in Tables 2 to 4 given below. Each of the thus prepared polymerization liquids was accommodated in a mold which has a thickness of 0.2 mm and which is formed of polypropylene. Photopolymerization was conducted by irradiating the mold accommodating the polymerization liquid, with a visible ray having a wavelength of 405 nm and an illumination intensity of 3 mW/cm$^2$ for 30 min, by using a fluorescent tube (TL 20W/03 RS AQUA CORAL, available from Philips Electronics Japan Ltd.). Thereafter, the thus obtained polymer was taken out of the mold, and immersed in distilled water for hydration. Appearance of the hydrated polymer was visually observed. Results of the observation are indicated in Tables 2 to 4.

TABLE 2

| | | Example 1 | Example 2 | Example 3 | Example 4 | Example 5 | Example 6 |
|---|---|---|---|---|---|---|---|
| Proportion (part by weight) | Kind of macromonomer | Macromonomer A | Macromonomer B | Macromonomer C | Macromonomer D | Macromonomer E | Macromonomer F |
| | Proportion | 35 | 35 | 35 | 35 | 35 | 35 |
| | TRIS | 25 | 25 | 25 | 25 | 25 | 25 |
| | N-MMP | 25 | 25 | 25 | 25 | 25 | 25 |
| | DMAA | 15 | 15 | 15 | 15 | 15 | 15 |
| | HMEPBT | 2 | 2 | 2 | 2 | 2 | 2 |
| | TPO | 0.3 | 0.3 | 0.3 | 0.3 | 0.3 | 0.3 |
| | Appearance | Transparent | Transparent | Transparent | Transparent | Transparent | Transparent |
| | | Example 7 | Example 8 | Example 9 | Example 10 | Example 11 | Example 12 |
| (part by | Kind of macromonomer | Macromonomer G | Macromonomer H | Macrmonomer A | Macromonomer B | Macromonomer C | Macromonomer D |
| | Proportion | 35 | 35 | 28 | 28 | 28 | 28 |
| | TRIS | 25 | 25 | 28 | 28 | 28 | 28 |
| | N-MMP | 25 | 25 | 34 | 34 | 34 | 34 |
| | DMAA | 15 | 15 | 10 | 10 | 10 | 10 |
| | HMEPBT | 2 | 2 | 2 | 2 | 2 | 2 |
| | TPO | 0.3 | 0.3 | 0.3 | 0.3 | 0.3 | 0.3 |
| | Appearance | Transparent | Transparent | Transparent | Transparent | Transparent | Transparent |
| | | Example 13 | Example 14 | Example 15 | Example 16 | | |
| Proportion (part by weight) | Kind of macromonomer | Macromonomer E | Macromonomer F | Macromonomer G | Macromonomer H | | |
| | Proportion | 28 | 28 | 28 | 28 | | |
| | TRIS | 28 | 28 | 28 | 28 | | |
| | N-MMP | 34 | 34 | 34 | 34 | | |
| | DMAA | 10 | 10 | 10 | 10 | | |
| | HMEPBT | 2 | 2 | 2 | 2 | | |
| | TPO | 0.3 | 0.3 | 0.3 | 0.3 | | |
| | Appearance | Transparent | Transparent | Transparent | Transparent | | |

TABLE 3

| | | Example 17 | Exampmle 18 | Example 19 | Example 20 | Example 21 | Example 22 | Example 23 |
|---|---|---|---|---|---|---|---|---|
| Proportion (part by weight) | Kind of macromonomer | Macromonomer F | Macromonomer H | Macromonomer F | Macromonomer H | Macromonomer I | Macromonomer J | Macromonomer K |
| | Proportion | 22 | 22 | 22 | 22 | 22 | 28 | 22 |
| | TRIS | 36 | 36 | 36 | 36 | 33 | 28 | 36 |
| | N-MMP | 17 | 17 | — | — | 25 | 34 | 22 |
| | NVP | — | — | 17 | 17 | — | — | — |
| | DMAA | 20 | 20 | 20 | 20 | 20 | 10 | 20 |
| | HMEPBT | 2 | 2 | 2 | 2 | 2 | 2 | 2 |
| | TPO | 0.3 | 0.3 | 0.3 | 0.3 | 0.3 | 0.3 | 0.3 |
| | Appearance | Transparent | Transparent | Transparent | Transparent | Transparent | Transparent | Transparent |

TABLE 4

| | | Comparative Example 1 | Comparative Example 2 | Comparative Example 3 | Comparative Example 4 | Comparative Example 5 | Comparative Example 6 |
|---|---|---|---|---|---|---|---|
| Proportion (part by weight) | Kind of macromonomer | Comparative Macromonomer b | Comparative Macromonomer c | Comparative Macromonomer d | Comparative Macromonomer e | Comparative Macromonomer c | Comparative Macromonomer e |
| | Proportion | 35 | 35 | 28 | 28 | 22 | 22 |
| | TRIS | 25 | 25 | 28 | 28 | 36 | 36 |
| | N-MMP | 25 | 25 | 34 | 34 | 17 | 17 |
| | DMAA | 15 | 15 | 10 | 10 | 20 | 20 |
| | Me-PEG-A | — | — | — | — | 5 | 5 |

TABLE 4-continued

| | Comparative Example 1 | Comparative Example 2 | Comparative Example 3 | Comparative Example 4 | Comparative Example 5 | Comparative Example 6 |
|---|---|---|---|---|---|---|
| HMEPBT | 2 | 2 | 2 | 2 | 2 | 2 |
| TPO | 0.3 | 0.3 | 0.3 | 0.3 | 0.3 | 0.3 |
| Appearance | Clouded | Clouded | Slightly clouded | Clouded | Clouded | Clouded |

As is apparent from the results indicated in Tables 2 to 4, it was recognized that the polymers obtained from the polymerization liquids prepared by using the polysiloxane-based macromonomers according to the invention were not clouded, whereas the polymers obtained from the polymerization liquids prepared by using the polysiloxane-based macromonomers which are outside the scope of the invention were clouded.

The invention claimed is:

1. A polysiloxane-based macromonomer for an ophthalmic lens, comprising:
   at least one polymerizable group,
   a polysiloxane chain having a siloxane unit as a repeating unit,
   a polyoxyethylene chain in which a number of repetition of an oxyethylene group is two or more, and
   a polyoxyalkylene chain having an oxyalkylene group other than the oxyethylene group as a repeating unit, wherein
      the polysiloxane chain, the polyoxyethylene chain and the polyoxyalkylene chain constitute a main chain of a molecule of the polysiloxane-based macromonomer,
      the at least one polymerizable group is bonded to the polysiloxane chain constituting the main chain of the molecule of the polysiloxane-based macromonomer, through at least one urethane bond, and
      an HLB value calculated according to the following formula is within a range from 0.7 to 6.0:

[HLB value]=$E/5$ wherein E represents a weight fraction (wt %) of the oxyethylene group in a molecule of the polysiloxane-based macromonomer.

2. The polysiloxane-based macromonomer for an ophthalmic lens according to claim 1, wherein the HLB value is within a range from 1.0 to 5.0.

3. The polysiloxane-based macromonomer for an ophthalmic lens according to claim 1, wherein the number of repetition of the oxyethylene group is within a range from 4 to 15.

4. The polysiloxane-based macromonomer for an ophthalmic lens according to claim 1, wherein the polyoxyalkylene chain is a polyoxypropylene chain having an oxypropylene group as a constituent unit.

5. The polysiloxane-based macromonomer for an ophthalmic lens according to claim 4, wherein a number of repetition of the oxypropylene group is within a range from 5 to 16.

6. An ophthalmic lens formed of a polymer of a polymerizable composition including the polysiloxane-based macromonomer for an ophthalmic lens according to claim 1.

7. A contact lens formed of a polymer of a polymerizable composition including the polysiloxane-based macromonomer for an ophthalmic lens according to claim 1.

8. The polysiloxane-based macromonomer for an ophthalmic lens according to claim 1, wherein the polysiloxane-based macromonomer is represented by the following general formula (I):

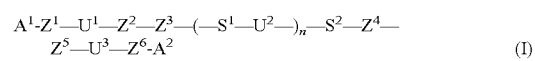

$$A^1\text{-}Z^1\text{—}U^1\text{—}Z^2\text{—}Z^3\text{—}(\text{—}S^1\text{—}U^2\text{—})_n\text{—}S^2\text{—}Z^4\text{—}Z^5\text{—}U^3\text{—}Z^6\text{-}A^2 \quad (I)$$

where
   n is 0 or an integer within the range from 1 to 10;
   $A^1$ is a group represented by a general formula (II):

$$Y^{21}\text{—}R^{21}\text{—} \quad (II)$$

where
      $Y^{21}$ represents an acryloyloxy group, a methacryloyloxy group, a vinyl group or an allyl group, independently of each other, and
      $R^{21}$ represents a direct bond or a linear or branched alkylene group having 2 to 6 carbon atoms, independently of each other;
   $A^2$ is a group represented by a general formula (III):

$$\text{—}R^{22}\text{—}Y^{22} \quad (III)$$

where
      $Y^{22}$ represents an acryloyloxy group, a methacryloyloxy group, a vinyl group or an allyl group, independently of each other, and
      $R^{22}$ represents a direct bond or a linear or branched alkylene group having 2 to 6 carbon atoms, independently of each other;
   each of $Z^1$, $Z^2$, $Z^3$, $Z^4$, $Z^5$ and $Z^6$ represents a direct bond or a polyoxyalkylene chain having an oxyalkylene group as a repeating unit, independently of one another, wherein at least one of $Z^1$ to $Z^6$ is the polyoxyethylene chain in which the number of repetition of the oxyethylene group is two or more, and at least one of $Z^1$ to $Z^6$ which is not the polyoxyethylene chain is the polyoxyalkylene chain having the oxyalkylene group other than the oxyethylene group as the repeating unit;
   $U^1$ is a group represented by a general formula (IV):

$$\text{-}E^{21}\text{-}X^{21}\text{—} \quad (IV)$$

and includes the urethane bond in the molecular chain of the polysiloxane-based macromonomer, where in the general formula (IV)
   $X^{21}$ represents an oxygen atom, and
   $E^{21}$ represents
      a —NHCO— group, wherein $E^{21}$ forms the urethane bond with $X^{21}$, or a divalent group derived from a diisocyanate selected from a group consisting of saturated aliphatic diisocyanates, unsaturated aliphatic diisocyanates, alicyclic diisocyanates and aromatic diisocyanates, wherein $E^{21}$ forms the urethane bond with each of $Z^1$ and $X^{21}$;

$U^2$ is a group represented by a general formula (VI):

  (VI)

and includes the urethane bond in the molecular chain of the polysiloxane-based macromonomer, where the general formula (VI)

each of $R^{41}$ and $R^{42}$ represents a linear or branched alkylene group having 2 to 6 carbon atoms, independently of each other, and each of $X^{41}$ and $X^{42}$ represents an oxygen atom or an alkylene glycol group, independently of each other, and $E^{41}$ represents a divalent group derived from a diisocyanate selected from the group consisting of saturated aliphatic diisocyanates, unsaturated aliphatic diisocyanates, alicyclic diisocyanates and aromatic diisocyanates, wherein $E^{41}$ forms the urethane bond with each of $X^{41}$ and $X^{42}$;

$U^3$ is a group represented by a general formula (VII):

  (VII)

and includes the urethane bond in the molecular chain of the polysiloxane-based macromonomer, where in the general formula (VII)

$X^{22}$ represents an oxygen atom, and $E^{22}$ represents the —NHCO— group, wherein $E^{22}$ forms the urethane bond with $X^{22}$, or a divalent group derived from a diisocyanate selected from the group consisting of saturated aliphatic diisocyanates, unsaturated aliphatic diisocyanates, alicyclic diisocyanates and aromatic diisocyanates, wherein $E^{22}$ forms the urethane bond with each of $Z^5$ and $X^{22}$; and each of $S^1$ and $S^2$, which are independent of each other, is a group represented by a general formula (V):

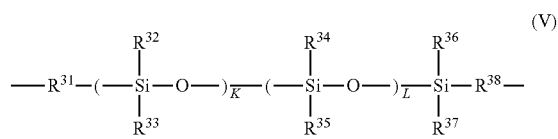  (V)

where each of $R^{31}$ and $R^{38}$ represents a linear or branched alkylene group having 2 to 6 carbon atoms, independently of each other, and each of $R^{32}$, $R^{33}$, $R^{34}$, $R^{35}$, $R^{36}$ and $R^{37}$ represents an alkyl group having 1 to 6 carbon atom(s), a fluorine-substituted alkyl group or a phenyl group, independently of one another, K is an integer within a range from 1 to 1500, and L is 0 or an integer within a range from 1 to 1500, wherein a sum of K and L:

$K+L$ is an integer within the range from 1 to 1500.

9. The polysiloxane-based macromonomer for an ophthalmic lens according to claim 1, wherein the polysiloxane-based macromonomer is represented by one of the following general formulas (VIII), (IX) and (XIII):

General Formula (VIII)

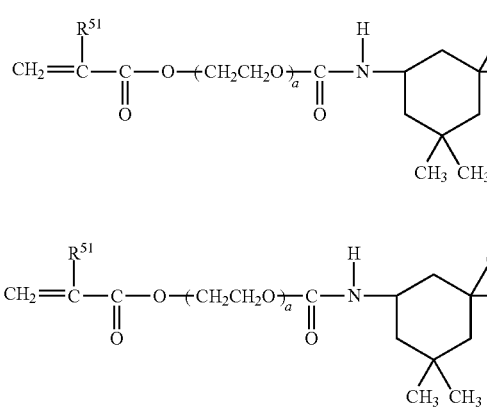

where $R^{51}$ represents a hydrogen atom or a methyl group, a is an integer not smaller than two, b is an integer not smaller than two, n is an integer within a range from 1 to 1500, and each of $R^{52}$ and $R^{53}$ is a hydrogen atom or a methyl group, wherein if $R^{53}$ is a methyl group then $R^{52}$ is a hydrogen atom, and if $R^{53}$ is a hydrogen atom then $R^{52}$ is a methyl group;

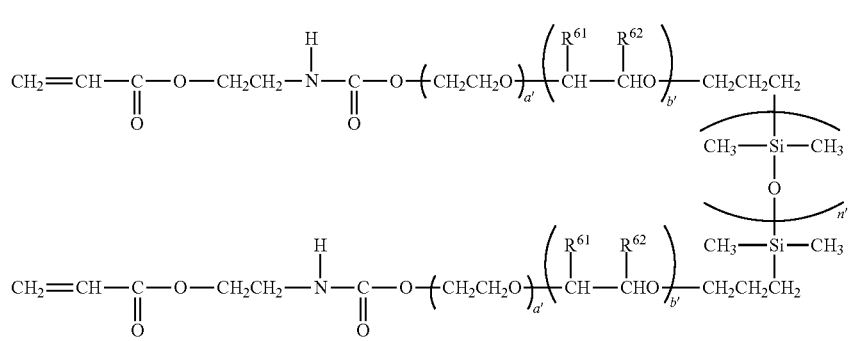

General Formula IX where
a' is an integer not smaller than two,
b' is an integer not smaller than two,
n' is an integer within a range from 1 to 1500, and
each of $R^{61}$ and $R^{62}$ is a hydrogen atom or a methyl group, wherein
if $R^{62}$ is a methyl group then $R^{61}$ is a hydrogen atom, and
if $R^{62}$ is a hydrogen atom then $R^{61}$ is a methyl group; and

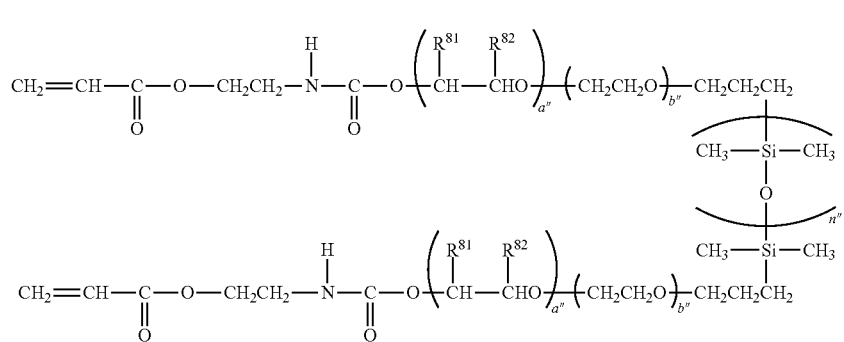

General Formula XIII where
a" is an integer not smaller than two,
b" is an integer not smaller than two,
n" is an integer within a range from 1 to 1500, and
each of $R^{81}$ and $R^{82}$ is a hydrogen atom or a methyl group, wherein
if $R^{82}$ is a methyl group then $R^{81}$ is a hydrogen atom, and
if $R^{82}$ is a hydrogen atom then $R^{81}$ is a methyl group.

10. The polysiloxane-based macromonomer for an ophthalmic lens according to claim 8, wherein the HLB value is within a range from 1.0 to 5.0.

11. The polysiloxane-based macromonomer for an ophthalmic lens according to claim 9, wherein the HLB value is within a range from 1.0 to 5.0.

* * * * *